United States Patent [19]

Evans et al.

[11] Patent Number: 4,673,737

[45] Date of Patent: Jun. 16, 1987

[54] 7-ACYLAMINO-(OR 7-AMINO)-3-TRIFLUOROMETHYLSULFONYLOXY-1-CARBA(1-DETHIA)-3-CEPHEM-4-CARBOXYLIC ACIDS AND ESTERS THEREOF

[75] Inventors: David A. Evans, Concord; Eric B. Sjogren, Arlington, both of Mass.

[73] Assignee: Harvard University, Cambridge, Mass.

[21] Appl. No.: 761,647

[22] Filed: Aug. 2, 1985

[51] Int. Cl.⁴ .......................................... C07D 471/04
[52] U.S. Cl. .................................. 540/205; 544/316; 544/362; 546/183
[58] Field of Search ................ 546/183; 514/299, 210; 544/316, 362; 540/205

[56] References Cited

U.S. PATENT DOCUMENTS 4,226,866 10/1980 Christensen et al. ............... 514/229
4,275,207 6/1981 Ratcliffe et al. .................... 546/183

FOREIGN PATENT DOCUMENTS 0154253 9/1985 European Pat. Off. .
642968 5/1984 Switzerland .
GB2041923A 9/1980 United Kingdom .

OTHER PUBLICATIONS

Evans et al, Tetrahedron Letters, vol. 26 (32), 3783–3790.
Evans, Chem. Abst., 104-5677b.
Hatanaka et al, Tetrahedron Letters, vol. 24 (44), 4837–4838.
Hirata et al, Chem. Abst. 93-239247t.
Application for Continuation Grant No. GM33328, Davis A. Evans, Harvard University, Feb. 16, 1984.
Application for Continuation Grant No. GM33328, Davis A. Evans, Harvard University, Mar. 13, 1985.

*Primary Examiner*—Donald G. Daus
*Assistant Examiner*—Cecilia Shen
*Attorney, Agent, or Firm*—William B. Scanlon; Leroy Whitaker

[57] ABSTRACT

7β-Acylamino-3-trifluoromethylsulfonyloxy-1-carba-3-cephem-4-carboxylic acid antibiotic compounds, esters and salts thereof, and the corresponding 7-amino and protected 7-amino 1-carbacephalosporins are provided. The 3-trifluoromethylsulfonyloxy-substituted 1-carbacephalosporins also are useful in a process for preparing 3-halo-1-carbacephalosporins which comprises reacting a 3-triflate ester with a lithium halide in an aprotic polar solvent.

18 Claims, No Drawings

7-ACYLAMINO-(OR 7-AMINO)-3-TRIFLUOROMETHYLSULFONYLOXY-1-CARBA(1-DETHIA)-3-CEPHEM-4-CARBOXYLIC ACIDS AND ESTERS THEREOF

The United States government has rights in this invention by virtue of Grant No. GM-33328 awarded by the National Institutes of Health.

BACKGROUND OF THE INVENTION

This invention relates to 1-carba(1-dethia)-3-cephem-4-carboxylic acids and derivatives thereof. In particular, it relates to 7-acylamino-(or 7-amino)-3-trifluoromethylsulfonyloxy-1-carba(1-dethia)-3-cephem-4-carboxylic acids and esters thereof and to a process for preparing 3-chloro and 3-bromo-1-carba(1-dethia)-3-cephem-4-carboxylic acids with the 3-trifluoromethylsulfonyloxy derivatives.

The 1-carba(1-dethia)-3-cephem-4-carboxylic acids, hereinafter 1-carbacephalosporins, possess the 4,6-bicyclo ring system represented by the following formula

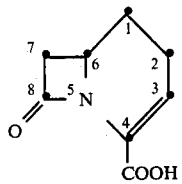

wherein the numbering of the cepham nomenclature system is used for convenience.

The preparation of 1-carbacephalosporins and C-3 substituted methyl derivatives thereof is taught broadly by Christensen et al., U.S. Pat. No. 4,226,866. Hirata et al., U.K. Patent Application No. 2041923 teach a process for preparing 3-H and 3-halo 1-carbacephalosporins, while Hatanaka et al., Tetrahedron Letters, 24, [No. 44], pp. 4837-4838 (1983), teach a process for preparing a 3-hydroxy-(±)-1-carbacephalosporin. Because of the importance of these newer β-lactam antibiotics, there is a need for better methods for their preparation and for 1-carbacephalosporins with enhanced potency against infectious and resistant microorganisms.

DETAILED DESCRIPTION

The 1-carbacephalosporin compounds provided by this invention are represented by the formula 1

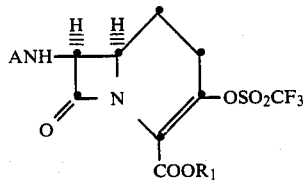

wherein A is hydrogen, an amino-protecting group, or an acyl group

wherein R is hydrogen; $C_1$-$C_6$ alkyl, $C_1$-$C_6$ alkyl substituted by cyano, carboxy, halogen, amino, $C_1$-$C_4$ alkoxy, $C_1$-$C_4$ alkylthio, or trifluoromethylthio; a phenyl or substituted phenyl group represented by the formula

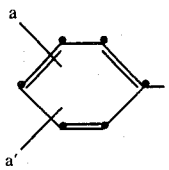

wherein a and a' independently are hydrogen, halogen, hydroxy, $C_1$-$C_4$ alkoxy, $C_1$-$C_4$ alkanoyloxy, $C_1$-$C_4$ alkyl, $C_1$-$C_4$ alkylthio, amino, $C_1$-$C_4$ alkanoylamino, $C_1$-$C_4$ alkylsulfonylamino, carboxy, carbamoyl, hydroxymethyl, aminomethyl, or carboxymethyl; a group represented by the formula

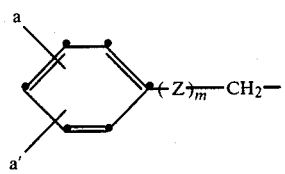

wherein a and a' have the same meanings as defined above, Z is O or S, and m is 0 or 1; a heteroarylmethyl group represented by the formula

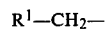

wherein $R^1$ is thienyl, furyl, benzothienyl, benzofuryl, indolyl, triazolyl, tetrazolyl, oxazolyl, thiazolyl, oxadiazolyl, thiadiazolyl, and such heteroaryl groups substituted by amino, hydroxy, halogen, $C_1$-$C_4$ alkyl, $C_1$-$C_4$ alkoxy, $C_1$-$C_4$ alkylsulfonylamino; a substituted methyl group represented by the formula

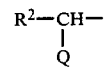

wherein $R^2$ is cyclohex-1,4-dienyl, or a phenyl group or substituted phenyl group represented by the formula

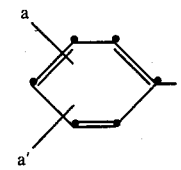

wherein a and a' have the above defined meanings, or $R^2$ is $R^1$ as defined above, and Q is hydroxy, $C_1$-$C_4$ alkanoyloxy, carboxy, sulfo, amino, or a substituted amino group represented by the formula

wherein R' is hydrogen or $C_1$-$C_3$ alkyl, R" is $C_1$-$C_4$ alkyl, furyl, thienyl, phenyl, halophenyl, nitrophenyl, styryl, halostyryl, nitrostyryl or a group

wherein R' is hydrogen or $C_1$–$C_3$ alkyl, and R''' is hydrogen, $C_1$–$C_3$ alkylsulfonyl, $C_1$–$C_3$ alkyl, or $C_1$–$C_4$ alkanoyl; or Q is a substituted amino group represented by the formula

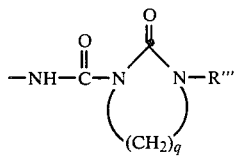

wherein R''' has the same meanings as defined above and q is 2 or 3; or Q is a substituted amino group represented by the formula

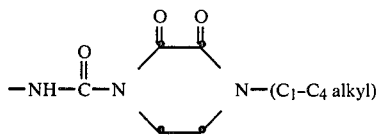

or a benzamido group represented by the formula

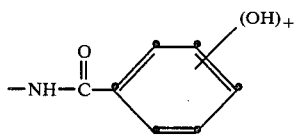

wherein t is 1 to 3; or R is a keto group or an oximino-substituted group represented by the formulae

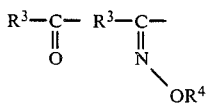

wherein $R^3$ is $R^1$ or $R^2$ as defined above and $R^4$ is hydrogen, $C_1$–$C_4$ alkyl, or a carboxy-substituted alkyl or cycloalkyl group represented by the formula

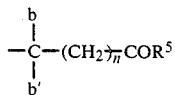

wherein b and b' independently are hydrogen, or $C_1$–$C_3$ alkyl, and b and b' when taken together with the carbon to which they are bonded form a 3- to 6-membered carbocyclic ring, and $R^5$ is hydroxy, $C_1$–$C_4$ alkoxy, amino, $C_1$–$C_4$ alkylamino, or di($C_1$–$C_4$ alkyl)amino, $R_1$ is hydrogen or a carboxy-protecting group; and when $R_1$ is hydrogen, the pharmaceutically acceptable non-toxic salts thereof.

The compounds represented by the formula 1, wherein A is an acyl group RCO and $R_1$ is hydrogen and the pharmaceutically acceptable non-toxic salts thereof, inhibit the growth of microorganisms pathogenic to man and animals. The compounds in esterified form ($R_1$=carboxy-protecting group) are useful in a process for preparing 3-chloro and 3-bromo-1-carba-3-cephem esters and acids as described hereinafter. Such 3-halo-1-carba-3-cephem-4-carboxylic acids and salts thereof are also antibiotics useful in the treatment of infectious diseases in man and animals.

In the above definition of the compounds represented by the formula 1, $C_1$–$C_6$ alkyl refers to the straight and branched chain alkyl groups such as methyl, ethyl, n-propyl, isopropyl, n-butyl, t-butyl, n-pentyl, n-hexyl, 3-methylpentyl, and like alkyl groups; $C_1$–$C_6$ alkyl substituted by cyano refers to cyanomethyl, cyanoethyl, 4-cyanobutyl, and the like; $C_1$–$C_6$ alkyl substituted by carboxy refers to such groups as carboxymethyl, 2-carboxyethyl, 2-carboxypropyl, 4-carboxybutyl, 5-carboxypentyl, and the like; $C_1$–$C_6$ alkyl substituted by halogen refers to chloromethyl, bromomethyl, 2-chloroethyl, 1-bromoethyl, 4-chlorobutyl, 4-bromopentyl, 6-chlorohexyl, 4-fluorobutyl, 3-fluoropropyl, fluoromethyl, and the like; $C_1$–$C_6$ alkyl substituted by amino refers to such groups as 2-aminoethyl, aminomethyl, 3-aminopropyl and 4-aminobutyl; $C_1$–$C_6$ alkyl substituted by $C_1$–$C_4$ alkoxy refers to methoxymethyl, 2-methoxyethyl, 2-ethoxyethyl, ethoxymethyl, 3-propoxypropyl, 3-ethoxybutyl, 4-t-butyloxybutyl, 3-methoxypentyl, 6-methoxyhexyl, and like group; $C_1$–$C_6$ alkyl substituted by $C_1$–$C_4$-alkylthio refers to such groups as for example methylthiomethyl, 2-methylthioethyl, 2-ethylthiopropyl, 4-methylthiobutyl, 5-ethylthiohexyl, 3-t-butylthiopropyl, and like groups; $C_1$–$C_6$ alkyl substituted by trifluoromethyl is exemplified by 2,2,2-trifluoroethyl, 3,3,3-trifluoropropyl, 4,4,4-trifluorobutyl, and the like; and $C_1$–$C_6$ alkyl substituted by trifluoromethylthio refers to, for example, trifluoromethylthiomethyl, 2-trifluoromethylthioethyl, 2-trifluoromethylthiopropyl, 4-trifluoromethylthiobutyl, 5-trifluoromethylthiohexyl, and like $C_1$–$C_6$ alkyl substituted groups.

When in the formula 1 R is a substituted phenyl group wherein the substituent(s) are represented by a and a', examples of such groups are halophenyl such as 4-chlorophenyl, 3-bromophenyl, 2-fluorophenyl, 2,4-dichlorophenyl, and 3,5-dichlorophenyl; hydroxyphenyl such as 2-hydroxyphenyl, 3-hydroxyphenyl, 4-hydroxyphenyl, 2,4-dihydroxyphenyl, and 3,4-dihydroxyphenyl; alkoxyphenyl, such as 2,6-dimethoxyphenyl, 4-methoxyphenyl, 3-ethoxyphenyl, 3,4-dimethoxyphenyl, 4-t-butyloxyphenyl, 4-methoxy-3-ethoxyphenyl, and 4-n-propoxyphenyl; alkanoyloxyphenyl such as 2-acetoxyphenyl, 4-propionoxyphenyl, 4-formyloxyphenyl, 4-acetoxyphenyl, 3-butyryloxyphenyl, and 3-acetoxyphenyl; alkylphenyl such as 4-methylphenyl, 2-methylphenyl, 2,4-dimethylphenyl, 3-t-butylphenyl, 4-ethylphenyl, 4-ethyl-3-methylphenyl, and 3,5-dimethylphenyl; alkylthiophenyl such as 4-methylthiophenyl, 3-n-butylthiophenyl, 2-ethylthiophenyl, 3,4-dimethylthiophenyl, and 3-n-propylthiophenyl; aminophenyl such as 2-aminophenyl, 4-aminophenyl, 3,5-diaminophenyl, and 3-aminophenyl; alkanoylamino such as 2-acetylamino, 4-acetylamino, 3-propionylamino, and 4-butyrylamino; alkylsulfonylamino such a 3-methylsulfonylamino, 4-methylsulfonylamino, 3,5-(dimethylsulfonylamino)phenyl, 4-n-butylsulfonylaminophenyl, and 3-ethylsulfonylaminophenyl; carboxyphenyl such as 2-, 3-, or 4-, carboxyphenyl, 3,4-dicarboxyphenyl, and 2,4-dicarboxyphenyl; carbamoylphenyl such as 2-carbamoylphenyl, 2,4-dicarbamoylphenyl, and 4-carbamoylphenyl; hydroxymethylphenyl such as 4-hydroxymethylphenyl and 2- hydroxymethylphenyl; aminomethylphenyl such as 2-aminomethylphenyl and 3-aminomethylphenyl; and carboxyphenyl such as 2-carboxymethylphenyl, 4-carboxymethylphenyl, and 3,4-dicarboxymethylphenyl; and the substituted phenyl groups bearing different substituents such as 4-chloro-3-methylphenyl, 4-fluoro-3-hydroxyphenyl, 3,5-dichloro-4-hydroxyphenyl, 4-hydroxy-3-chlorophenyl, 4-hydroxy-3-methylphenyl, 4-ethyl-3-hydroxyphenyl, 4-methoxy-3-hydroxyphenyl, 4-t-butyloxy-2-hydroxyphenyl, 4-acetylamino-3-methoxyphenyl, 3-amino-4-ethylphenyl, 2-aminomethyl-4-chlorophenyl, 2-hydroxymethyl-3-methoxyphenyl, 2-hydroxymethyl-4-fluorophenyl, 2-acetoxy-4-aminophenyl, 4-acetoxy-3-methoxyphenyl, 3-isopropylthio-4-chlorophenyl, 2-methylthio-4-hydroxymethylphenyl, 4-carboxy-3-hydroxyphenyl, 4-ethoxy-3-hydroxyphenyl, 4-methylsulfonylamino-2-carboxyphenyl, 4-amino-3-chlorophenyl, and 2-carboxymethyl-4-hydroxyphenyl.

Examples of RCO— groups of the formula 1 wherein R is a group represented by the formula

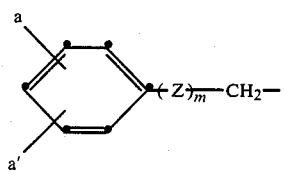

with m=0 are: phenylacetyl, 4-hydroxyphenylacetyl, 4-chlorophenylacetyl, 3,4-dichlorophenylacetyl, 4-methoxyphenylacetyl, 3-ethoxyphenylacetyl, 2-aminomethylphenylacetyl, 3-carboxyphenylacetyl, 4-acetoxyphenylacetyl, 3-aminophenylacetyl, and 4-acetylaminophenylacetyl; and with m=1 and Z=O, phenoxyacetyl, 4-chlorophenoxyacetyl, 4-fluorophenoxyacetyl, 3-aminophenoxyacetyl, 3-hydroxyphenoxyacetyl, 2-methoxyphenoxyacetyl, 2-methylthiophenoxyacetyl, 4-acetylaminophenoxyacetyl, 3,4-dimethylphenoxyacetyl, and 3-hydroxymethylphenoxyacetyl; and with m=1 and Z=S, phenylthioacetyl, 4-chlorophenylthioacetyl, 3,4-dichlorophenylthioacetyl, 2-fluorophenylthioacetyl, 3-hydroxyphenylthioacetyl, and 4-ethoxyphenylthioacetyl.

Examples of $R^1$—$CH_2CO$— groups of the formula 1 wherein $R^1$ is a heteroaryl group are: 2-thienylacetyl, 3-thienylacetyl, 2-furylacetyl, 2-benzothienylacetyl, 2-benzofurylacetyl, indol-2-ylacetyl, 1H-tetrazol-1-ylacetyl, oxazol-2-ylacetyl, oxazol-4-ylacetyl, thiazol-4-ylacetyl, 2-aminothiazol-4-ylacetyl, 1,3,4-oxadiazol-2-ylacetyl, 1,3,4-thiadiazol-2-ylacetyl, 5-ethyl-1,3,4-thiadiazol-2-ylacetyl, and like heteroaryl groups optionally substituted by amino, $C_1$-$C_4$ alkylsulfonylamino, hydroxy, halo, $C_1$-$C_4$ alkyl or $C_1$-$C_4$-alkoxy groups.

Examples of RCO— groups of the formula 1 compounds wherein R is a substituted methyl group represented by the formula $R^2$—CH(Q)— and Q is amino, carboxy, hydroxy, or sulfo, are 2-carboxy-2-phenylacetyl, 2-carboxy-2-(4-hydroxyphenyl)acetyl, 2-amino-2-phenylacetyl, 2-amino-2-(4-hydroxyphenyl)acetyl, 2-amino-2-(3-chloro-4-hydroxyphenyl)acetyl, 2-amino-2-(cyclohex-1,4-dien-1-yl)acetyl, 2-hydroxy-2-phenylacetyl, 2-formyloxy-2-phenylacetyl, 2-sulfo-2-phenylacetyl, 2-sulfo-2-(4-methylphenyl)acetyl, and 2-acetoxy-2-(3-hydroxyphenyl)acetyl, 2-amino-2-(2-thienyl)acetyl, 2-amino-2-(3-benzothienyl)acetyl, 2-amino-2-(1H-tetrazol-1-yl)acetyl, 2-hydroxy-2-(1,3,4-thiadiazol-2-yl)acetyl, 2-amino-2-(2-aminothiazol-4-yl)acetyl, 2-carboxy-2-(2-thienyl)acetyl, 2-carboxy-2-(benzothien-2-yl)acetyl, and 2-hydroxy-2-(benzofur-2-yl)acetyl; and when Q is a substituted amino group represented by the formula

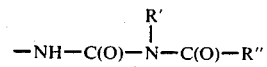

examples of such acyl groups are 2-(N-methyl-N-benzoylcarbamoylamino)-2-phenylacetyl, 2-(N-methyl-N-cinnamoylcarbamoylamino)-2-(2-furyl)acetyl, 2-(N,N-dimethylcarbamoylureido)-2-(4-chlorophenyl)acetyl, 2-[N-methyl-N-(2-chlorocinnamoyl)carbamoylamino]-2-(2-thienyl)acetyl, and 2-(N-ethyl-N-acetylcarbamoylamino)-2-(4-hydroxyphenyl)acetyl; and when Q is a substituted amino group represented by the formula

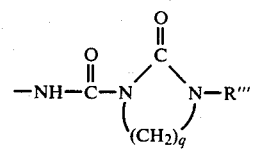

examples of acyl group R(CO)— are 2-[(3-methylimidazolidin-2-one-1-yl)carbonylamino]-2-phenylacetyl, 2-[(3-acetylimidazolidin-2-one-1-yl)carbonylamino]-2-phenylacetyl, 2-[(3-methylsulfonylimidazolidin-2-one-1-yl)-2-(2-thienyl)acetyl, and 2-[(3-acetylhexahydropyrimidin-2-one-1-yl)carbonylamino]-2-phenylacetyl; and when Q is a hydroxy-substituted benzamido group represented by the formula

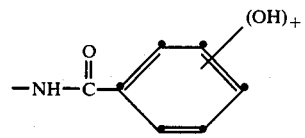

examples of such acyl groups are 2-(2,4-dihydroxybenzamido)-2-phenylacetyl, 2-(4-hydroxybenzamido)-2-(4-hydroxyphenyl)acetyl, 2-(3,4-dihydroxybenzamido)-2-(2-aminothiazol-4-yl)acetyl, 2-(3,5-dihydroxybenzamido)-2-(3-thienyl)acetyl, and 2-(2-hydroxybenzamido)-2-(2-benzofuryl)acetyl.

Examples of RCO acyl groups of the compounds represented by formula 1 when R is a keto group or an oximino-substituted group represented by the formulae

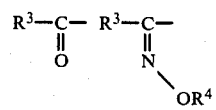

are the keto groups 2-oxo-2-phenylacetyl, 2-oxo-2-(2-thienyl)acetyl, 2-oxo-2-(2-aminothiazol-4-yl)acetyl; and oximino-substituted groups 2-phenyl-2-methoxyiminoacetyl, 2-(2-thienyl)-2-ethoxyiminoacetyl, 2-(2-furyl)-2-methoxyiminoacetyl, 2-(2-benzothienyl)-2-carboxymethoxyiminoacetyl, 2-(2-thienyl)-2-(2-carboxyethoxy)iminoacetyl, 2-(2-amino-1,2,4-thiadiazol-4-yl)-2-methoxyiminoacetyl, 2-(2-aminothiazol-4-yl)-2-methoxyiminoacetyl, 2-(2-chlorothiazol-4-yl)-2-methoxyiminoacetyl, 2-(2-aminothiazol-4-yl)-2-(2-carboxyprop-2-yl)oxyiminoacetyl, 2-(2-aminothiazol-4-yl)-2-(2-carbamoylprop-2-yl)oxyiminoacetyl, and 2-(5-amino-1,3,4-thiadiazol-2-yl)-2-methoxyiminoacetyl.

The carboxy-protecting group $R_1$ is a conventional carboxy-blocking group used in the β-lactam antibiotic art and serves the function of blocking the acidic carboxy group while reactions are carried out at other sites in the molecule. Such groups are used for the temporary protection or blocking of the carboxy group. Examples of such groups are t-butyl, haloalkyl groups, e.g. 2,2,2-trichloroethyl, 2-iodoethyl, allyl, 1,1-dimethylprop-2-yne-1-yl, benzyl, substituted benzyl, e.g. 4-nitrobenzyl, and 4-methoxybenzyl, diphenylmethyl, trialkylsilyl or mixed alkylarylsilyl groups, e.g. trimethylsilyl, triethylsilyl, dimethylphenylsilyl, β-trimethylsilylethyl, and β-methylsulfonylethyl.

The 3-trifluoromethylsulfonyloxy-1-carbacephalosporins represented by the formula 1 wherein A is RCO or an amino-protecting group are prepared by the O-acylation of the corresponding 3-hydroxy-1-carbacephalosporin ester as illustrated below.

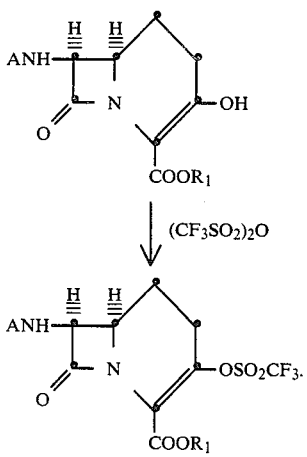

wherein $R_1$ is a carboxy-protecting group. During the acylation any reactive groups in the side chain group A also capable of acylation are desirably protected. For example, any amino group substituents are protected with a conventional amino-protecting group to prevent amide formation in competition with the desired ester formation. The acylation is carried out in an inert solvent at a temperature between about 0° C. and about 35° C. in the presence of a tertiary amine. Amines which are suitable include triethylamine, tri-n-butylamine, pyridine, diethyl-t-butylamine, diisopropylethylamine, and like amines. Hindered trialkylamines are preferred. The acylating reagent can be trifluoromethanesulfonic anhydride (triflic anhydride) or trifluoromethanesulfonyl chloride (triflic chloride) or other suitable acid derivatives of trifluoromethanesulfonic acid. Inert solvents useful in the process are the halogenated hydrocarbons such as chloroform, methylene chloride, trichloroethane and the like; ether solvents such as tetrahydrofuran, esters such as ethyl acetate; or other inert solvents, e.g. acetonitrile.

The triflic esters are recovered from the reaction mixture by conventional isolation methods, e.g. by extraction. Following the esterification the C4 carboxy-protecting group $R_1$ is removed to provide free acid 3-triflic ester where in formula 1 $R_1$ is hydrogen. Alternatively, the carboxy-protecting group can be left intact and the diester used in the process described hereinafter for the preparation of the corresponding 3-chloro-1-carbacephalosporin.

The 3-trifluoromethanesulfonyloxy compounds represented by the formula 1 are also prepared by the N-acylation of a 7-amino-3-trifluoromethanesulfonyloxy-1-carba-3-cephem-4-carboxylic acid ester (formula 1, A=hydrogen) with the carboxylic acid RCOOH wherein R has the same meanings as defined in formula 1. An active derivative of the carboxy group of the acid is desirably used in the acylation. For example, acid halides, acid azides and active esters or acid anhydrides may be used in the acylation. Likewise, the free acid may be coupled with the amine in the presence of a dehydrating agent such as a carbodiimide, e.g. dicyclohexycarbodiimide.

Active esters of the carboxylic acid such as those formed with N-hydroxysuccinimide and hydroxybenztriazole or those formed with the haloformates, e.g. ethyl chloroformate and isobutyl chloroformate, may be used.

The N-acylation of a 7-amino-3-trifluoromethylsulfonyloxy-3-cephem ester is illustrated below

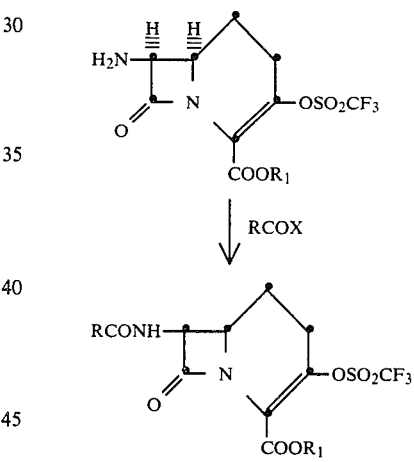

wherein R has the same meanings as defined for formula 1, $R_1$ is a carboxy-protecting group, and X represents OH (free acid), OCOR (anhydride), or a reactive derivative, for example chloro.

The N-acylations are carried out by using the methods employed for the acylation of the cephalosporin nuclei such as 7-ACA and 7-ADCA. In an example of the acylation benzyl 7-amino-3-trifluoromethylsulfonyloxy-1-carba-3-cephem-4-carboxylate in acetonitrile is treated with phenoxyacetyl chloride in the presence of an acid-binding agent such as triethylamine or pyridine to provide benzyl 7-phenoxyacetylamino-3-trifluoromethylsulfonyloxy-1-carba-3-cephem-4-carboxylate.

The compounds represented by the formula 1 wherein Q is a substituted amino group are obtained by N-acylation of a compound wherein Q is amino. For example, the compound represented by the formula

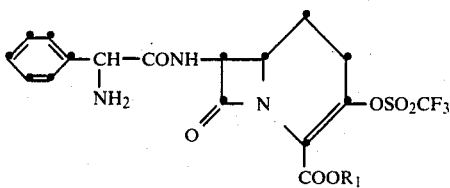

wherein R₁ is a carboxy-protecting group, is acylated in the presence of an acid scavenger with a compound represented by the formulae

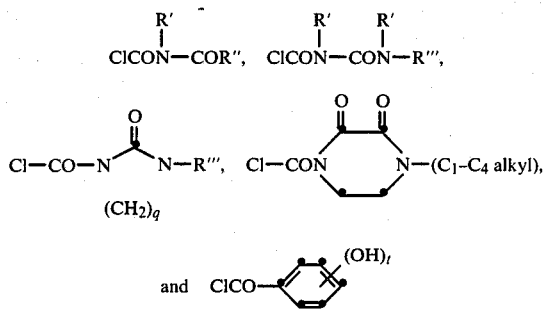

and ClCO—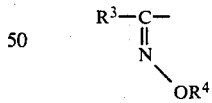

wherein R', R'', R''', t and q have the same meanings as defined for formula 1.

Examples of 3-trifluoromethylsulfonyloxy-1-carba-3-cephem-4-carboxylic acids and esters of the invention represented by the formula 1 are shown below.

| R | R₁ |
|---|---|
| H | benzyl |
| CH₃— | benzyl |
| NCCH₂— | benzyl |
| Cl—CH₂— | pMB |
| CF₃SCH₂— | H |
| 2,6-dimethoxyphenyl | H |
| 4-methylphenyl | H |
| 4-chlorophenyl | benzyl |
| 3-hydroxyphenyl | benzyl |
| phenoxymethyl | benzyl |
| phenoxymethyl | H |
| phenoxymethyl | pNB |
| 4-chlorophenoxymethyl | H |
| 4-hydroxyphenoxymethyl | H |
| phenylthiomethyl | H |
| benzyl | H |
| benzyl | benzyl |
| 4-chlorophenylthiomethyl | H |
| 4-fluorophenylthiomethyl | H |
| 4-chlorobenzyl | H |
| 2-aminomethylbenzyl | H |
| 3-carboxymethylbenzyl | H |
| 2-thienylmethyl | benzyl |
| 2-thienylmethyl | H |
| 2-thienylmethyl | pNB |
| 2-benzothienylmethyl | H |
| 2-benzofurylmethyl | H |
| 1,3,4-thiadiazol-2-ylmethyl | H |
| 1,3,4-oxadiazol-2-ylmethyl | H |
| 1H—tetrazol 1-ylmethyl | H |
| α-aminobenzyl | pMB |
| α-aminobenzyl | 2,2,2-trichloroethyl |
| α-aminobenzyl | H |
| α-amino-(4-hydroxybenzyl) | H |
| α-amino-(3-methylsulfonylaminobenzyl) | H |
| α-hydroxybenzyl | H |
| α-formyloxybenzyl | H |
| α-carboxybenzyl | H |
| α-carboxy-(4-hydroxybenzyl) | H |
| α-sulfobenzyl | H |
| α-[N³—methyl-N³—(2-chloro-benzoyl)ureido]benzyl | H |
| α-[N³—(methylaminocarbonyl)N³—methyl ureido] 4-hydroxybenzyl | H |
| α-(3-acetylimidazolidin-2-one-1-yl carbonylamino)benzyl | H |
| α-(3-methylsulfonylimidazolidin-2-one-1-ylcarbonylamino)benzyl | H |
| α-(4-ethylpiperizin-2-dione-1-yl carbonylamino)benzyl | H |
| α-(4-hydroxybenzamido)benzyl | H |
| α-(3,4-dihydroxybenzamido)benzyl | H | and when R₁ is H the pharmaceutically acceptable non-toxic salts thereof.

A preferred group of compounds of the invention are represented by the formula 1 when R is benzyl or phenoxymethyl. A further preferred group are represented when R is R²—CH(Q-)—, and in particular, when Q is amino or substituted amino. Examples of such compounds are 7β-(α-aminophenylacetylamino)-3-trifluoromethylsulfonyloxy-1-carba-3-cephem-4-carboxylic acid, 7β-[α-amino-α-(4-hydroxyphenyl)acetylamino]-3-trifluoromethylsulfonyloxy-1-carba-3-cephem-4-carboxylic acid, 7β-[α-amino-α-(3-hydroxy-4-chlorophenyl)acetylamino]-3-trifluoromethylsulfonyloxy-1-carba-3-cephem-4-carboxylic acid, and the pharmaceutically acceptable salts thereof. The above-named compounds having an asymmetric carbon to which the amino group is attached in the 7-position side chain are preferably in the D-form.

The preferred compounds wherein Q is amino are prepared by employing known acylation methods used in the β-lactam antibiotic art. For example, phenylglycyl chloride hydrochloride can be used to acylate the trimethylsilyl ester of 7-amino-3-trifluoromethylsulfonyloxy-1-carba-3-cephem-4-carboxylic acid in non-aqueous media in the presence of an acid-binding agent.

Also, the t-butyloxycarbonyl protected phenylglycine is converted to the active derivative with a haloformic acid ester such as ethyl chloroformate and the derivative used to acylate the 7-amino-1-carba nucleus ester, e.g. the benzyl ester.

Another group of preferred compounds are represented by the formula 1 when R is an oximino group represented by the formula $$R^3-\underset{\underset{OR^4}{\overset{\|}{N}}}{C}-$$

In particular, compounds wherein the oximino group has the syn configuration are preferred, especially when R³ is thiazolyl, e.g. 2-aminothiazol-4-yl, 2-halothiazol-4-yl, and 2-methylthiazol-4-yl; and R₄ is C₁–C₄-alkyl or a carboxy-substituted C₁–C₄-alkyl group.

The compounds represented by the formula 1 wherein R₁ is hydrogen form salts with inorganic and organic bases. Salts such as the alkali and alkaline earth metal salts, e.g. the sodium, potassium and calcium salts, are formed with the respective alkali or alkaline earth metal hydroxides, carbamates and bicarbamates. Amine salts are formed with basic amines such as benzylamine, dibenzylamine, ethanolamine, diethanolamine, propanolamine, procaine, and dicyclohexylamine. These salt forms of the 1-carba-3-cephem compounds are useful in preparing pharmaceutically acceptable formulations of the antibiotics.

The 7-amino-1-carbacephalosporin nucleus compounds used in the above-described N-acylation are obtained with 7-protected amino nucleus compounds by removing the protecting group. This invention also provides preferred 7-amino- and 7-(protected amino)-3-trifluoromethylsulfonyloxy-1-carba-3-cephem nucleus compounds represented by the formula 2

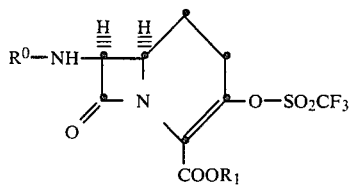

wherein $R^o$ is hydrogen or an amino-protecting group, and $R_1$ is hydrogen or a carboxy-protecting group. Amino-protecting groups represented by $R^o$ are the conventional protecting or blocking groups used in the β-lactam antibiotic art for the temporary protection of the amino group function while reactions at other sites in the molecule are carried out. Examples of suitable protecting groups are formyl, trichloroacetyl, tribromoacetyl, trityl, an alkyl, cycloalkyl, or aryloxycarbonyl group such as ethoxycarbonyl, t-butyloxycarbonyl, trichloroethoxycarbonyl, cyclopentyloxycarbonyl, benzyloxycarbonyl, p-nitrobenzyloxycarbonyl, and diphenylmethoxycarbonyl; allyloxycarbonyl, a bicyclooxycarbonyl group such as adamantyloxycarbonyl or bicycloheptyloxycarbonyl; or other conventional amino-protecting group. Preferred amino-protecting groups $R^o$ are represented by the formula

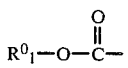

wherein $R^o{}_1$ is $C_1$-$C_4$-alkyl, $C_2$-$C_4$ alkenyl, $C_3$-$C_7$ cycloalkyl, benzyl, nitrobenzyl, halobenzyl or methoxybenzyl.

Preferred amino-protecting groups are benzyloxycarbonyl, p-nitrobenzyloxycarbonyl, and t-butyloxycarbonyl.

The 7-amino(or amino-protected)-3-trifluoromethylsulfonyloxy nucleus compounds represented by the formula 2 are prepared with the corresponding 3-hydroxy-1-carbacephalosporin obtained as described in copending application Ser. No. 755,982, filed July 17, 1985 (attorney Docket No. X-6605). As described therein, an asymmetric process for the preparation of 3-hydroxy-1-carbacephalosporins is provided. According to the process, a 3β-[4(S)-aryloxazolidin-2-one-3-yl]azetidin-2-one is prepared and converted asymmetrically to a 7-amino-protected or 7-acylamino 3-hydroxy-1-carbacephalosporin. The azetidinone-2 is represented by the formula

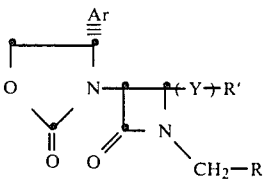

wherein Ar is phenyl, $C_1$-$C_4$ alkylphenyl, halophenyl, $C_1$-$C_4$ alkoxyphenyl, naphthyl, thienyl, furyl, benzothienyl, or benzofuryl; R is phenyl, $C_1$-$C_4$ alkylphenyl, $C_1$-$C_4$ alkoxyphenyl, or halophenyl; Y is —CH=CH—, or —CH$_2$—CH$_2$—; and R' is phenyl, $C_1$-$C_4$ alkylphenyl, $C_1$-$C_4$ alkoxyphenyl, halophenyl, furyl or naphthyl.

Preferred azetidinones are represented by the formula 1 wherein Ar and R are phenyl or substituted phenyl, and R' is phenyl, substituted phenyl, or furyl. Examples of such preferred compounds are 1-benzyl-3β-[4(S)-phenyloxazolidin-2-one-3-yl]-4β-styrylazetidin-2-one, 1-benzyl-3β-[4(S)-phenyloxazolidin-2-one-3-yl]-4β-(3-methoxystyryl)azetidin-2-one, and 1-benzyl-3β-[4(S)-phenyloxazolidin-2-one-3-yl]-4β-[2-(2-furyl)ethenyl]-azetidin-2-one.

The azetidinones are obtained by the cycloaddition of a 4(S)-aryloxazolidin-2-one-3-ylacetyl halide and an imine formed with a benzylamine and a 3-arylacrolein. The acid halide is converted in situ with a trialkylamine to the corresponding homochiral ketene. The ketene and imine upon cycloaddition provide the azetidinone. Alternatively, the ketene can be generated with the anhydride of the oxazolidinone acetic acid and trifluoroacetic acid, or with phosphoryl chloride or phosphoryl bromide. The cycloaddition reaction is a key step in the asymmetric process for the preparation of 1-carba-(1-dethia)cephalosporins.

The 4(S)-aryloxazolidin-2-one-3-ylacetyl halide employed in the cyclization is obtained with an L-arylglycine represented by the formula 1a

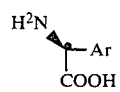

wherein Ar has the same meanings as defined above. The preparation is illustrated in the following reaction scheme.

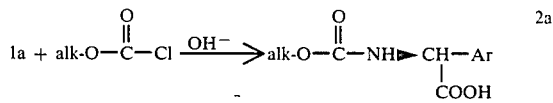

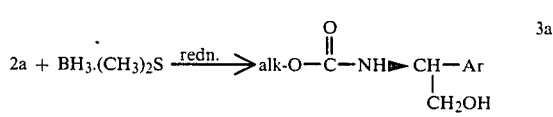

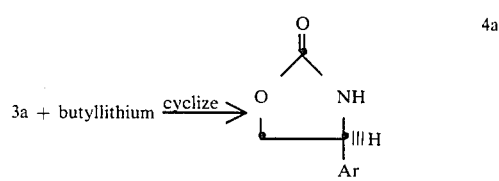

 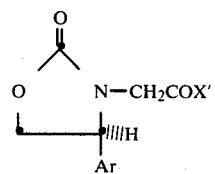

In the above scheme "alk" refers to $C_1$–$C_4$ alkyl e.g. methyl, ethyl, n-propyl, and t-butyl; X refers to halogen, preferably chloro or bromo; X' is chloro, bromo, trifluoroacetoxy; or —OP(=O)$X_2$ wherein X is halogen; and Ar has the same meanings as previously defined.

In carrying out the preparation of the 4-aryloxazolidinone 4a the L-arylglycine is first converted to the carbamate 2a. The arylglycine is dissolved in aqueous base by utilizing only the amount of base needed to form the soluble salt plus a small excess. The solution is cooled to a temperature between about 0° C. and about 10° C. and non-stoichiometric amounts of the haloformate are added in several portions with stirring. Additional base is added to redissolve the arylglycine and additional haloformate is added portionwise with stirring. This process is repeated in the cold until an excess of the stoichiometric amount of haloformate has been added and carbamate formation is completed. The reaction is preferably carried out as rapidly as possible. Bases such as the alkali metal hydroxides, e.g. sodium hydroxide and potassium hydroxide are best used. Preferably 3N sodium hydroxide is used. The L-carbamate derivative 2a is recovered from the reaction mixture by acidification and extraction of the precipitated carbamate with a water immiscible solvent e.g. a halogenated hydrocarbon solvent such as dichloromethane.

The L-carbamate 2a is reduced with excess borane-dimethylsulfide in tetrahydrofuran at a temperature between about 20° C. and about 40° C. to provide the L-alcohol 3a. The borane-dimethylsulfide reagent is added to a solution of the carbamate acid in tetrahydrofuran cooled to about 0° C. and the mixture is stirred at the temperature range, conveniently at room temperature, for about 10 hours to 20 hours. The excess borane is destroyed by quenching the mixture with water and 3a is recovered by concentrating the mixture by evaporation, diluting the concentrate with more water if necessary, and extracting 3a with a water immiscible solvent such as methylene chloride. The recovered 3a is of sufficient purity to use directly in the cyclization to 4a, however, it may be further purified prior to use by recrystallization.

The L-alcohol 3a is then cyclized to the (S)-4-aryloxazolidin-2-one (4a) in an inert solvent with n-butyllithium or an alkali metal alkoxide such as lithium or sodium ethoxide. n-Butyllithium is the preferred base and is generally used in less than the stoichiometric amount. The reaction is carried out for from 2 to 8 hours at a temperature between about 25° C. and about 65° C. and preferably at about 55° C. Suitable inert solvents are tetrahydrofuran, 1,2-dimethoxyethane and like ethers. After completion of the cyclization, the reaction mixture is treated with acetic acid in an amount corresponding to the amount of base used, and is concentrated. The oxazolidin-2-one(4a) is recovered from the concentrate by extraction with a suitable organic solvent such as methylene chloride, chloroform, or trichloroethane.

The (S)-4-aryloxazolidin-2-one (4a) is N-alkylated with a haloacetic acid ester, the ester deesterified, and the acid converted to the acyl halide 5a.

The alkylation of 4a with the haloacetic acid ester is carried out in dimethylformamide or tetrahydrofuran with sodium hydride to provide the (S)-4-aryloxazolidin-2-one-3-ylacetic acid ester. The haloacetic acid ester is represented by the formula X—$CH_2$COOalk in the foregoing reaction scheme, wherein X is chloro or bromo and alk is $C_1$–$C_4$ alkyl. Preferably, alk is t-butyl or ethyl. Examples of haloacetic acid esters are t-butyl bromoacetate, ethyl bromoacetate, methyl chloroacetate, t-butyl chloroacetate, methyl bromoacetate, isopropyl bromoacetate, and like esters. Preferred halo esters are t-butyl bromoacetate and ethyl bromoacetate.

The deesterification of the oxazolidinone acetic acid ester is achieved by standard deesterification procedures. For example, the t-butyl ester group is removed upon treatment of the ester with trifluoroacetic acid while other lower alkyl esters such as the ethyl ester can be saponified.

The oxazolidinone acetic acid is converted to the acid halide (5a, X'=halogen), preferably the acid chloride, the anhydride formed with trifluoroacetic acid (X'=O-COC$F_3$), or with a phosphoryl halide (X'=—O—P(=O)$X_2$). The acid halide, preferably the chloride, is a preferred source of the ketene for use in the subsequent cyclo-addition reaction. The acid chloride is obtained for example with oxalyl chloride in an inert solvent such as benzene, toluene, or xylene. Other conventional acid halide forming reagents may be used.

The (S)-4-aryloxazolidin-2-one-3-ylacetyl halide or anhydride is the functionalized form of the chiral auxiliary moiety used to form the β-lactam ring of the azetidinone intermediates represented by the above formula.

The acetyl halide (5a) is allowed to react with the imine formed with a benzylamine and a 3-arylacrolein to form the 1-benzyl-3β-[(S)-4-aryloxazolidin-2-one-3-yl]-4β-(2-arylvinyl)azetidinone (formula 1, Y=—CH=CH). A minor amount of isomeric cycloaddition product is also formed. The cycloaddition reaction is illustrated in the following reaction scheme

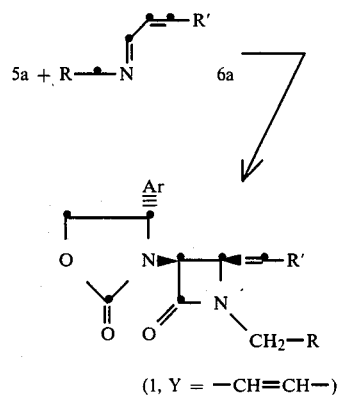

wherein R, R' and Ar have the same meanings as defined above.

The reaction is carried out at a temperature between about −78° C. and about 25° C. in an inert organic solvent, such as methylene chloride, chloroform, toluene, or a di- or trichloroethane in the presence of a tri-($C_1$–$C_4$ alkyl)amine. A solution of the imine (6a) is added to a solution of 5a in an inert solvent containing the tri-($C_1$–$C_4$ alkyl)amine in an amount in excess of the stoichiometric amount. The tri-($C_1$–$C_4$ alkyl)amine is added to the solution of 5a prior to addition of the imine 6a. The acid derivative 5a and the amine are mixed at a temperature between about $-80°$ C. and about $-50°$ C. to form in situ the ketene. The imine 6a is then added to form the azetidinone. Conveniently, the solvent for the imine is the solvent in which it was prepared as described hereinbelow. Such solvents as benzene, toluene, and the xylenes are suitable. Following the addition of the imine, the reaction is warmed and maintained at about 0° C. for from 2 to 4 hours. The mixture of the major isomer and the minor isomer is recovered from the reaction mixture as follows. The reaction mixture is diluted with a water immiscible organic solvent such as methylene chloride or chloroform and is first washed with a weak acid such as tartaric acid or citric acid followed by a wash with saturated aqueous alkali metal bicarbonate. After drying, the washed mixture is evaporated to dryness. Most often the major isomer can be crystallized from the residue from ethyl acetate-hexanes (ca 30% hexanes by volume). Alternatively, the major isomer can be separated from the minor isomer by chromatography over silica by using step-wise elution or gradient elution. Step-wise elution with ethyl acetate-methylene chloride with a percentage ethyl acetate by volume of from ca 20% will generally elute the azetidinone while increased polarity (ca 40%–50% ethyl acetate by volume) will elute the minor component. After chromatography the azetidinone can be recrystallized to enhance its purity.

The imine 6a employed in the cycloaddition is obtained by condensing a 3-arylacrolein with benzylamine or a substituted benzylamine in a suitable solvent. The water produced during the reaction is removed either by using a drying agent or by azeotropic distillation. A small excess over the stoichimetric amount of the acrolein is preferably used. Drying agents such as magnesium sulfate or molecular sieves are suitable. Organic solvents such as diethyl ether or an aromatic hydrocarbon such as benzene or toluene can be employed.

The condensation to form the imine proceeds rapidly at a temperature between about 25° C. and 65° C. in the presence of a drying agent or during azeotropic removal of water.

Examples of 3-arylacroleins which can be used are represented by the formula

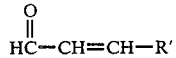

wherein R' is phenyl, $C_1$–$C_4$alkylphenyl, $C_1$–$C_4$ alkoxyphenyl, halophenyl, furyl or naphthyl. Examples of such aldehydes are cinnamaldehyde, 4-methylcinnaldehyde, 3-ethylcinnamaldehyde, 4-ethoxycinnamaldehyde, 3-methoxycinnamaldehyde, 3-t-butyloxycinnamaldehyde, 3-ethoxycinnamaldehyde, 3-bromocinnamaldehyde, 2-(furyl)acrolein, 2-(2-naphthyl)acrolein, and like aldehydes.

Examples of benzylamines useful in the imine formation are benzylamine and the $C_1$–$C_4$ alkyl, $C_1$–$C_4$ alkoxy, and halo-substituted benzylamines such as 4-methylbenzylamine, 3-chlorobenzylamine, 3,4-dichlorobenzylamine, 4-methoxybenzylamine, 2-bromobenzylamine, 3-ethylbenzylamine, 3,4-dimethylbenzylamine, 2,4-dimethylbenzylamine, 4-chloro-3-methylbenzylamine, 4-isopropylbenzylamine, 4-t-butylbenzylamine, and the like.

The imine 6a can be employed in the cycloaddition reaction without prior isolation. For example, the reaction mixture in which the imine is prepared may be used directly in the cycloaddition.

The azetidinone represented by the formula wherein Y is —CH═CH— and R' is an m-alkoxyphenyl group, is a valuable intermediate in a process provided by this invention for the asymmetric preparation of 1-carbacephalosporins. In particular the process comprises the preparation of 1-carba-3-hydroxy-3-cephem-4-carboxylic acid esters.

According to the process the (S)-4-aryloxazolidin-2-one-3-ylacetyl halide (5a) is reacted in the cycloaddition reaction described above with the imine (6a), formed with a benzylamine and a m-alkoxycinnamaldehyde, to provide the azetidinone represented by the above formula wherein Y is —CH═CH— and R' is a m—$C_1$–$C_4$ alkoxyphenyl group. The azetidinone is hydrogenated to the corresponding 4β-[2-m-alkoxyphenyl)ethyl]-azetidinone, and the latter is reduced with lithiumammonia in the presence of t-butyl alcohol to effect reduction of the phenyl ring, removal of the chiral auxiliary and the 1-benzyl group to provide a 3β-amino-4β-[2-(5-alkoxycyclohex-1,4-dienyl)ethyl]azetidinone. The 3-amino group of the azetidinone is protected with a conventional amino-protecting group and the 3β-protected-aminoazetidinone is subjected to ozonolysis to yield the β-keto ester $C_1$–$C_4$ alkyl 5-[3β-(protected amino)azetidin-2-one-4β-yl]-3-oxopentanoate.

The β-keto ester ozonolysis product is converted to the α-diazo derivative and the diazo derivative is cyclized with Rhodium II to provide the 3-hydroxy-1-carbacephalosporin ester.

The process is illustrated in the following reaction scheme.

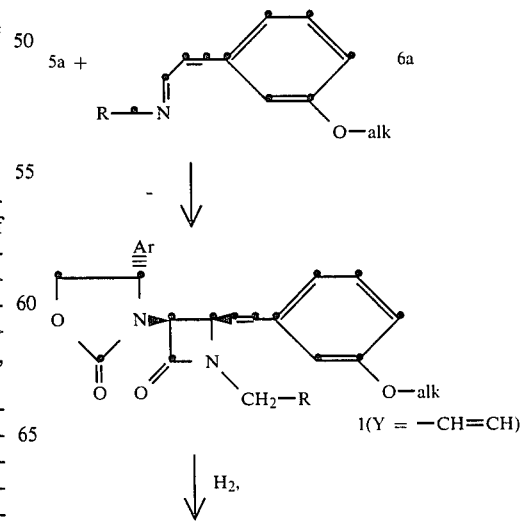

-continued

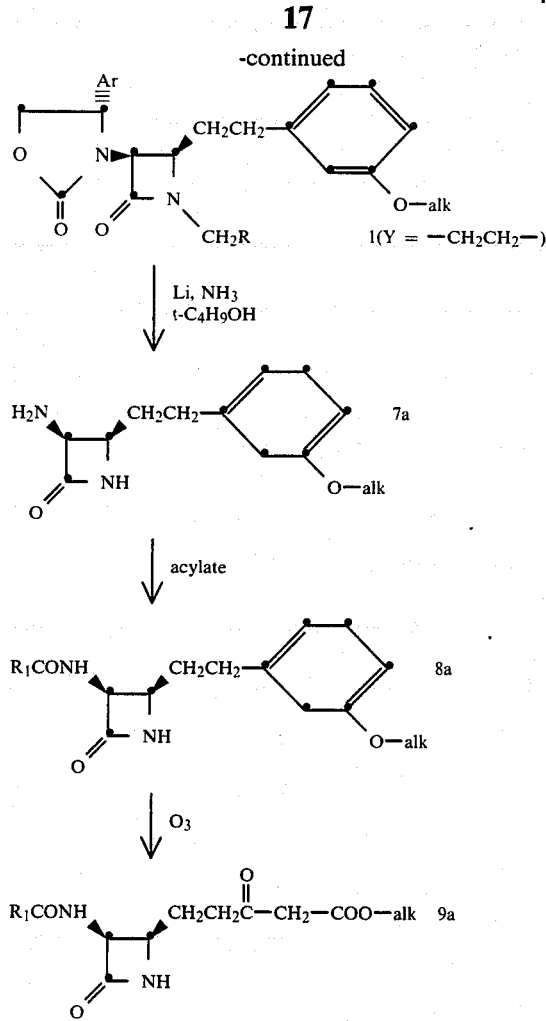

It will be appreciated with reference to the foregoing reaction scheme that the imine 6a is structurally selective in the process. The m-alkoxyphenyl group of the imine ultimately provides the alkyl β-ketoester 9a via ozonolysis of the 5-alkoxycyclohexa-1,4-diene 8a which in turn is provided by the lithium in ammonium reduction of the azetidinone wherein Y=—CH$_2$—CH$_2$—.

According to this process the azetidinone (Y=—CH=CH—) is hydrogenated over a palladium catalyst such as a supported palladium catalyst, e.g. 5% or 10% palladium on carbon, barium carbonate, or other suitable support. The reduction can be carried out at atmospheric pressure, or at somewhat elevated pressures, in an inert solvent at room temperature. Inert solvents such as methylene chloride, di- or trichloroethane, tetrahydrofuran, methyl alcohol, ethyl alcohol, or ethyl acetate may be used.

The 4β-[2-(m-alkoxyphenyl)ethyl]azetidinone is reduced to the 3β-amino-4β-[2-(5-alkoxycyclohex-1,4-dienyl)ethyl]azetidin-2-one (7a) with lithium in liquid ammonia containing t-butyl alcohol. The reduction is carried out at a temperature between about −30° C. and about −90° C. and preferably at between about −70° C. and about −80° C. The reduction is carried out by dissolving lithium in liquid ammonia and cooling the solution to about −50° C. and about −90° C. An excess of t-butyl alcohol is added followed by the addition of a solution of the azetidinone in an inert solvent. The solution of the azetidinone may contain t-butyl alcohol as a cosolvent. Suitable solvents for the azetidinone include tetrahydrofuran, dimethoxyethane, or like solvent.

After the solution of the azetidinone is added, the reduction mixture is stirred for about 30 minutes to about 2 hours. On small laboratory size reactions, the reduction is allowed to stir in the cold for about 30 minutes while with large scale reductions in manufacture somewhat longer reduction time may be required for complete reduction to the diene 7a.

The reduction effects the removal of the chiral auxiliary moiety, incorporated via the cyclo-addition with 6a, leaving the 3-amino group. The reduction also effects removal of the 1-benzyl or 1-substituted benzyl group.

The 3-aminoazetidinone 7a can be isolated from the reduction mixture and used in the next step after amino group protection as shown in the reaction scheme. Alternatively, and preferably in the process context, 7a is acylated in the same reaction vessel to provide the acylated aminoazetidinone 8a. Following the reduction the reaction mixture is treated with sufficient benzene to discharge the blue color of the mixture. Ammonium acetate is added to the mixture and the bulk of the ammonia is distilled off. The solvent and any remaining ammonia are evaporated. The residue 7a is treated with a water miscible organic solvent such as tetrahydrofuran and the mixture or solution is acidified to a pH between about 7 and about 9. The solution of 7a is then treated with an acylating agent to provide the 3β-acylamino-4β-[2-(5-alkoxycyclohex-1,4-dienyl)ethyl]-azetidinone 8a. The 3β-amino group is acylated to protect its integrity during the subsequent ozonolysis step in the process.

The acylating agent may be formed with any carboxylic acid, the acyl residue of which is stable in the subsequent ozonolysis step of the process. The carboxylic acid can be for example an alkylcarboxylic acid such as acetic acid, propionic acid, butyric acid and the like; an arylcarboxylic acid such as benzoic acid, napthoic acid, which may be optionally substituted by lower alkyl, lower alkoxy, or halogen; or an arylacetic acid such as phenylacetic acid, phenoxyacetic acid, phenylthioacetic acid, and such acids optionally substituted. The desired carboxylic acid for use in the acylation is converted to an active derivative such as the acid chloride, acid anhydride on an active ester formed with a haloformate such as a C$_1$-C$_4$ alkyl chloroformate, e.g. ethyl chloroformate and iso-butyl chloroformate.

The acylating agent also can be an aryloxycarbonyl halide such as benzyloxycarbonyl chloride or p-nitrobenzyloxycarbonyl chloride.

Preferred acylating agents are represented by the formula

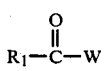

wherein R$_1$ is C$_1$-C$_6$ alkyl; a phenyl group

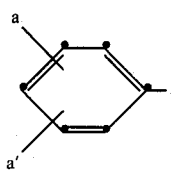

wherein a and a' independently are hydrogen, $C_1$-$C_4$ alkyl, $C_1$-$C_4$ alkoxy or halogen; a group represented by the formula

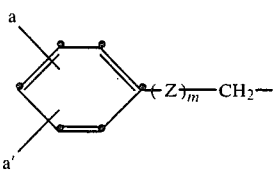

wherein Z is O or S, m is 0 or 1, and a and a' have the same meanings as defined above; or $R_1$ is $R^o_1O$ wherein $R^o_1$ represents $C_1$-$C_4$ alkyl, $C_5$-$C_7$ cycloalkyl, benzyl, nitrobenzyl, methoxybenzyl, or halobenzyl; and W is chloro, bromo, or an anhydride forming group represented by the formula

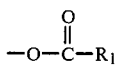

wherein $R_1$ has the same meanings as defined above.

Examples of acyl halides represented by the above formula are acetyl chloride, acetyl bromide, butyryl chloride, propionyl chloride, benzoyl chloride, 4-chlorobenzoyl chloride, 4-methylbenzoyl chloride, phenoxyacetyl chloride, 4-chlorophenoxyacetyl chloride, phenylacetyl chloride, 3-ethylphenylacetyl bromide, phenylmercaptoacetyl chloride, 4-chlorophenylmercaptoacetyl chloride, benzyloxycarbonyl chloride, cyclohexyoxycarbonyl chloride, cyclopentyloxycarbonyl chloride, ethoxycarbonyl chloride, and the like.

Examples of anhydrides represented by the above formula are benzoic acid anhydride, phenoxyacetic acid anhydride, phenylacetic acid anhydride, p-chlorophenoxyacetic acid anhydride, phenylmercaptoacetic acid anhydride, di-t-butyl dicarbonate, dibenzyl dicarbonate, di-(p-nitrobenzyl) dicarbonate, di-ethyl dicarbonate, di-cyclohexyl dicarbonate, and like anhydrides.

The N-acylated reduction product 8a is recovered from the mixture by extraction and is purified by chromatography over silica.

The 3-acylaminoazetidinone 8a is then converted to the β-keto ester 9a by ozonolysis. The ozonolysis is preferably carried out in 50% methyl alcohol in dichloromethane or other suitable solvent mixture, at a temperature between about −5° C. and about −80° C. The ozone is passed into the solution of the diene 8a until the reaction is complete. The ozone is most conveniently obtained from a conventional ozone generator in a stream of air. The completion of the ozonolysis may be determined by the use of a diene indicator such as solvent red (Sudan III, Aldrich Chemical Company). Following completion any ozonide and excess ozone is destroyed in the cold with dimethyl sulfide or other suitable reducing agent such as a sulfite or phosphite and the product 9a is recovered from the mixture. For example, the reaction mixture is allowed to warm to room temperature, is poured into brine and the product is extracted with a water immiscible solvent such as methylene chloride. The β-keto ester 9a may be further purified by chromatography over silica.

The β-keto ester 9a is then converted to the 7-acylamino-1-carba(1-dethia)-3-hydroxy-3-cephem ester 11a via diazo compound 10a, and cyclization of the diazo ester to the 1-carbacephalosporin with rhodium II.

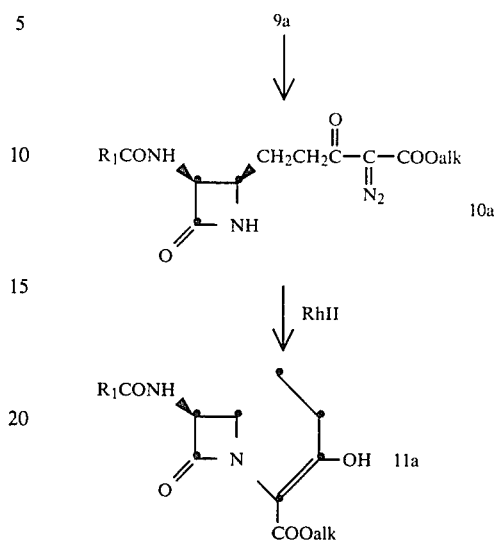

The β-keto ester 9a is best converted to the diazo ester 10a in an inert solvent such as acetonitrile, dichloromethane, trichloroethane, or the like, with p-toluenesulfonyl azide (tosyl azide) in the presence of a hindered tertiary amine, e.g. diisopropylethylamine. The reaction is carried at conveniently at room temperature. Generally the tosyl azide is used in an excess of the stoichiometric amount while the amine is used in an amount of about one-fourth of the stoichiometric amount. The diazo ester is recovered from the reaction mixture by partitioning the mixture between a water immiscible solvent such as methylene chloride and brine containing some tartaric acid or citric acid. The diazo ester is obtained in purified form from the extract via chromatography over silica and recrystallization.

The ester moiety "alk" of 10a becomes the ester group of the 1-carbacephalosporin 11a upon cyclization as shown in the reaction scheme. Ester groups such as the lower n-alkyl groups e.g. methyl, and ethyl, are less readily removed form the carboxy function than other groups. From a synthetic point of view, it may be desirable to form a 1-carbacephalosporin 11a wherein the ester group is a conventional carboxy-protecting group more readily removed than methyl or ethyl. A further aspect of the copending application provided a process for the transesterfication of the ester group (alk) of 10a to diazo ester 10b as shown below.

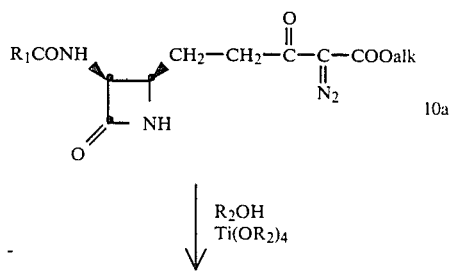

-continued

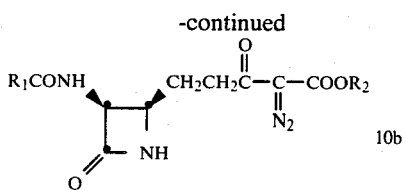
10b wherein $R_1$ and alk have the previously defined meanings and $R_2$ is allyl, 2,2,2-trichloroethyl, 2,2,2-tribromoethyl, β-tri($C_1$-$C_4$ alkyl)silylethyl, benzyl, $C_1$-$C_4$ alkylbenzyl, $C_1$-$C_4$ alkoxybenzyl, nitrobenzyl, or chlorobenzyl.

The process is carried out by mixing an excess of the alcohol, $R_2OH$, with titanium tetraisopropoxide and removing isopropyl alcohol by evaporation. The diazo ester, 10a, is added to the solution of the $Ti(OR_2)_4$ in excess alcohol, and an inert solvent if necessary, and the solution is maintained at a temperature between about 25° C. and about 45° C. until transesterification is complete.

Inert solvents which may be used are, for example, methylene chloride, di- or trichlorethane, chloroform, acetonitrile, tetrahydrofuran, or dioxane. When benzyl alcohol is used in the process to form the $R_2$ ester group it also may serve as a solvent for the process.

The diazo ester 10a or the diazo ester 10b obtained via the transesterification process is then cyclized to 1-carbacephalosporin 11a with rhodium II acetate in chloroformat the reflux temperature. The reaction is heated for about 15 minutes to about one hour and the 7-acylamino-3-hydroxy-1-carba(1-dethia)-3-cephem-carboxylic acid ester is recovered as such from the reaction mixture or is converted to a derivative which is then isolated.

The 3-hydroxy 1-carbacephalosporin ester may be recovered from the reaction mixture by first diluting the mixture with water or brine, acidifying the mixture, and then extracting the mixture with a solvent such as ethyl acetate or methylene chloride. The extract is washed, dried and evaporated to provide the product. The product may be further purified by chromatography and recrystallization.

In a preferred embodiment of the process L-phenylglycine (1a, Ar=phenyl) is converted to the ethylcarbamate with ethyl chloroformate, the carbamate acid is reduced with borane-dimethyl sulfide to L-1-ethoxycarbonylamino-1-phenylethanol (3a, alk=ethyl), and the phenylethanol is cyclized with n-butyllithium to (S)-4-phenyloxazolidin-2-one 4a. The latter is converted to 5a via alkylation with ethyl bromoacetate, saponification, and treatment of the acid with oxalyl chloride.

The (S)-4-phenyloxazolidin-2-one-3-ylacetyl chloride is condensed with the imine formed with benzylamine and m-methoxycinnamaldehyde (form 6a, alk=methyl, R=phenyl) to form the azetidinone 1, Ar=phenyl, alk=methyl). Catalytic reduction of 1 over 5% Pd—C provides azetidinone, (Y=CH$_2$—CH$_2$—) which on reduction on lithium in liquid ammonia and t-butyl alcohol yields the 3-aminoazetidinone (7a, alk=methyl). Without isolation, the 3-aminozetidinone is acylated with di-(t-butyl) dicarbonate to form the 3-t-butyloxycarbonylaminoazetidinone (8a, $R_1$=t-butyloxy, alk=methyl). Ozonolysis of the 3-t-BOC amino protected diene product in 50% methyl alcohol in dichloromethane provides the β-keto methyl ester 9a. The β-keto methyl ester is reacted in acetonitrile with tosyl azide in the presence of diisopropylethylamine to provide the diazo methyl ester (10a, $R_1$=t-butyloxy, alk=methyl). The transesterification of the diazo methyl ester to the corresponding benzyl ester is carried out in excess benzyl alcohol with titanium tetra-isopropoxide with heating at about 36° C. for 42 hours. The diazo benzyl ester is treated in refluxing chloroform with rhodium (II) acetate to provide benzyl 7β-(t-butyloxycarbonylamino)-3-hydroxy-1-carba(1-dethia)-3-cephem-4-carboxylate.

The 3-trifluoromethylsulfonyloxy-1-carba-3-cephem compounds represented by the formula 1 wherein A and $R_1$ are other than hydrogen are useful in a process for preparing 3-chloro or 3-bromo-1-carba-3-cephem compounds. According to the process a 3-triflate ester represented by the formula 3

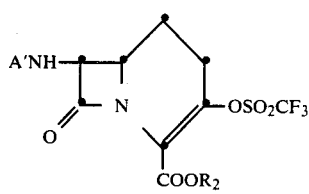
3 is reacted in an aprotic polar solvent at a temperature between about 60° C. and about 95° C. with a lithium halide, LiX", to form a 3-halo-1-carba-3-cephem compound represented by the formula 4

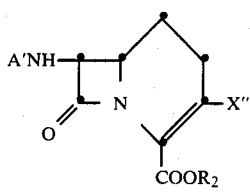
4 wherein A' is an amino-protecting group or an acyl group RCO wherein R has the same meanings as defined for formula 1, $R_2$ is a carboxy-protecting group, and X" is chloro or bromo.

Aprotic polar solvents which can be used are dimethylformamide, dimethylacetamide, N-methylpyrrolidone, acetonitrile, and like solvents. Dimethylformamide is a preferred solvent.

Preferably the process is carried out at a temperature between about 75° C. and about 85° C. with an excess of the stoichiometric amount of the lithium halide salt.

The carboxy-protecting ester group $R_2$ (formula 3) is a conventional carboxy-protecting ester group and preferably one which is not sterically hindered. Examples of such groups are benzyl and substituted benzyl groups such as 4-methoxybenzyl, 4-nitrobenzyl, 4-methylbenzyl, 3,5-dimethylbenzyl, and 4-chlorobenzyl; silyl esters such as trialkylsilyl ester, e.g. trimethylsilyl; and halo-substituted alkyl esters such as 2,2,2-trichloroethyl, 2,2,2-tribromoethyl, and 2-iodoethyl. Hindered ester groups such as the t-butyl ester group appear to inhibit the displacement of the $CF_3SO_3$ group by the halide ion owing to their bulk resulting in lower yields of the 3-halo product. A preferred ester group is the benzyl or a substituted benzyl ester group.

Following completion of the process the 3-halo-1-carba-3-cephem ester is recovered from the reaction mixture by conventional isolation methods and is purified by chromatography.

During the process any amino groups present in the starting material are desirably protected. For example, when in the compound represented by the formula 1 Q is an amino group or, when there is an amino or aminomethyl substituent attached to the phenyl ring when R is a substituted benzyl or phenyl group, an aminoprotected derivative is desirably used on the starting material in the process. In an example of the process, benzyl 7β-phenoxyacetylamino-3-trifluoromethylsulfonyloxy-1-carba-3-cephem-4-carboxylate is dissolved in dimethylformamide and an excess (3-4 molar excess) of lithium chloride is added. The solution is heated to a temperature of about 80° C. with stirring for about 5–6 hours. The progress of the reaction can be followed by thin layer chromatography of a small aliquot of the reaction mixture removed from time to time. When the reaction is completed the mixture is diluted with a water immiscible organic solvent, washed with water, dried, and evaporated. The crude product, benzyl 7β-phenoxyacetylamino-3-chloro-1-carba-3-cephem-4-carboxylate, is purified by chromatography, e.g. over silica gel.

The following Examples are provided to further illustrate the invention.

Preparation of benzyl
7β-(t-butyloxycarbonylamino)-3-hydroxy-1-carba-3-cephem-4-carboxylate (S)-4-Phenyloxazolidin-2-one To a stirred, 0° C. solution of L-phenylglycine (25.3 g, 167.4 mmol) in 60 mL of 3N aqueous NaOH was added ethyl chloroformate (8 mL) in several portions. Additional 3N aqueous NaOH (35 mL) was added to redissolve the precipitated phenylglycine, followed by ethyl chloroformate (4 mL). This process was continued with 3N aqueous NaOH (65 mL) and ethyl chloroformate (8 mL, total of 20 mL, 209 mmol) over a period of ca. 10 minutes. After stirring for 1 hour at 0' C. the solution was acidified with 6M $H_2SO_4$, and the precipitated carbamate was extracted into 8% isopropanol in dichloromethane (2×300 mL). The combined organic layers were dried ($Na_2SO_4$) and concentrated to afford 37.3 g of N-ethoxycarbonyl L-phenylglycine as a white solid. The carbamate was dissolved in 170 mL of THF, cooled to 0° C., treated with borane-dimethylsulfide (33.5 mL of a 10M solution), and stirred at room temperature for 17 hours. Excess borane was cautiously quenched with water (100 mL), and the bulk of the THF removed under reduced pressure. The white slurry was diluted with additional water (350 mL) and then extracted with dichloromethane (2×500 mL). The combined organic layers were washed with 100 mL of saturated aqueous $NaHCO_3$, dried ($Na_2SO_4$), and concentrated to give 27.4 g of (S)-2-ethoxycarbonylamino-2-phenylethanol as a white solid. The crude alcohol was dissolved in 200 mL of THF, cooled to 0° C., and treated with n-butyllithium in hexane (6 mL of a 2M solution). After heating at 55° C. for 6 hours, the solution was treated with acetic acid (1 ml) and concentrated. The residue was dissolved in dichloromethane (300 mL), washed with 100 mL of brine, dried ($Na_2SO_4$), and concentrated to a white solid. Recrystallization from toluene gave 17.14 g (63%) of (S)-4-phenyloxazolidin-2-one; mp 132°–133° C.; $[\alpha]_D^{20} +49.5°$ (c=2.1, $CHCl_3$); IR ($CHCl_3$) 3460, 3020, 1760, 1500, 1480, 1460, 1400, 1230 $cm^{-1}$; $^1$HNMR δ7.45–7.30 (m, 5, ArH), 6.42 (br s, 1, NH), 4.96 (br t, 1, J=7.8 Hz, OC$\underline{H}_2$CH), 4.72 (t, 1, J=8.6 Hz, one of OC$\underline{H}_2$CH), 4.17 (dd, 1, J=6.7, 8.7 Hz; one of OC$\underline{H}_2$CH).

Anal. Calcd for $C_9H_9NO_2$: C, 66.24; H, 5.56. Found: C, 66.16; H, 5.62.

(S)-4-Phenyloxazolidin-2-one-3-ylacetic acid

To a stirred, 0° C. solution of (S)-4-phenyloxazoldin-2-one (1.07 g, 6.54 mmol) in 15 mL of THF was added sodium hydride (0.32 g of a 60% oil dispersion, 8.0 mmol). When gas evolution had ceased (ca. 10 minutes), ethyl bromoacetate (0.87 mL, 7.8 mmol) was added. After 2 hours at 0° C., the mixture was treated with 50 mL of 2N aqueous NaOH, stirred rapidly for 1 hour at room temperature, and then partitioned between hexane (50 mL) and water (50 mL). The aqueous layer was separated, acidified with 6M aqueous $H_2SO_4$, and extracted with dichloromethane (2'200 mL). The combined organic phases were dried ($Na_2SO_4$) and concentrated to a thick oil, which was dissolved in 4 mL of warm toluene, seeded, and allowed to crystallize overnight; filtration gave 1.33 g (92%) of (S)-4-phenyloxazolidin-2-one-3-ylacetic acid; mp 106°–108° C.; $[\alpha]_D^{22} +173°$ (c=2.0, $CHCl_3$); IR ($CHCl_3$) 3500–2500 (v. br), 1760 (br), 1480, 1460, 1430, 1230 $cm^{-1}$; $^1$H NMR δ11.2 (br s, 1, COOH), 7.47–7.25 (m, 5, ArH), 5.05 (t, 1, J=8.4 Hz, OC$\underline{H}_2$CH), 4.72 (t, 1, J=8.8 Hz, one of OC$\underline{H}_2$CH), 4.32 (d 1, J=18.4 Hz, one of NC$\underline{H}_2$), 4.17 (t, 1, J=8.4 Hz, one of OC$\underline{H}_2$CH), 3.41 (d, 1, J=18.4 Hz, one of NC$\underline{H}_2$).

Anal. Calcd for $C_{11}H_{11}NO_4$: C, 59.72; H, 5.01. Found: C, 59.83; H, 5.00.

(S)-4-phenyloxazolidin-2-one-3-ylacetyl chloride

A 250 mL round bottom flask fitted with a reflux condensor and a $CaSO_4$ drying tube was charged with (S)-4-phenyloxazolidin-2-one-3-ylacetic acid (5.3 g, 23.96 mmol) and 60 mL of toluene. The suspension was treated with oxalyl chloride (3.2 mL, 36.7 mmol) and stirred at 60° C. for 3 hours. At this point gas evolution had ceased and the reaction was homogeneous. Removal of solvent under reduced pressure afforded the title acid chloride as a thick oil.

Preparation of imine formed from benzylamine and 3-methoxycinnamaldehyde

To a solution of 3-methoxycinnamaldehyde (4.27 g, 26.33 mmol) in 40 mL of toluene was added benzylamine (2.73 mL, 25.01 mmol). The solution was warmed briefly to ca. 40° C.; and upon cooling became cloudy from released water. Argon flushed 4A molecular sieves (18 g, freshly activated) were added and the mixture was allowed to stand at room temperature for 16 hours. This solution of imine was used directly in the subsequent cyclization.

Formation of
1-benzyl-3β-[(S)-4-phenyloxazolidin-2-one-3-yl]-4β-(3-methoxystyryl)azetidin-2-one The oxazolidinone acid chloride was dissolved in dichloromethane (70 mL), cooled to −78° C., and treated with triethylamine (5.0 mL, 35.9 mmol). A fine, heavy precipitate formed over 15 minutes. To this mixture was added, via cannula, the toluene solution of the imine prepared as described above. The sieves from the imine solution were washed with dichloromethane (2×10 mL), and each wash added to the reaction. The cold bath was removed, the reaction warmed and maintained at 0° C. for 2 hours. The mixture was poured into 200 mL of dichloromethane, washed with 0.5M tartaric acid and saturated aqueous NaHCO$_3$ (50 mL each), dried (Na$_2$SO$_4$), and concentrated to a reddish oil. Crystallization from ca. 150 mL of 30% hexanes in ethyl acetate gave 6.87 g of the title compound as white needles. Chromatography of the mother liquor on 170 g of silica with 20% ethyl acetate in dichloromethane gave an additional 1.9 g of the azetidinone (total 8.77 g, 80%). The minor isomer was obtained by further elution with 40% ethyl acetate in dichloromethane and was then purified by chromatography on silica with 30% hexanes in ethyl acetate.

Major isomer, the title compound: mp 142°-143° C.; $[\alpha]_D^{22}+46.4°$ (c=1.0, CHCl$_3$); IR (CHCl$_3$) 3020, 1760, 1600, 1410 cm$^{-1}$; $^1$H NMR (CDCl$_3$) δ7.45-6.75 (m, 14, ArH), 6.45 (d, 1, J=16 Hz, ArCH=CH), 5.81 (dd, 1, J=16, 8.9 Hz, ArCH=CH), 4.88 (dd, 1, J=8.9, 7.4 Hz, OCH$_2$CH), 4.61 (t, 1, J=8.9 Hz, one of OCH$_2$CH), 4.55 (d, 1, J=5 Hz, C$_3$H), 4.53 (d, 1, J=14.7 Hz, one of ArCH$_2$), 4.23-4.12 (m, 3, one of ArCH$_2$, one of OCH$_2$CH, C$_4$H), 3.82 (s, 3, OCH$_3$).

Anal. Calcd for C$_{28}$H$_{26}$N$_2$O$_4$: C, 73.99; H, 5.77. Found: C, 74.06; H, 5.74.

By using the method described in Example 1, the imine prepared from benzylamine and cinnamaldehyde, and 4(S)-phenyloxazolidin-2-one-3-ylacetyl chloride there was prepared 1-benzyl-3β-[4(S)-phenyloxazolidine-2-one-3-yl]-4β-styrylazetidine-2-one: mp 186.5°-187.5° C.; $[\alpha]_D^{22}=+56.9°$ (c=1.7, CHCl$_3$); IR (CHCl$_3$) 3010, 1760, 1500, 1460, 1410 cm$^{-1}$; $^1$H NMR (CDCl$_3$) δ7.45-7.10 (m, 15, ArH), 6.48 (d, 1, J=16 Hz, CH=CH—Ar), 5.87 (dd, 1, J=9, 16 Hz, CH=CH—Ar), 4.88 (dd, 1, J=7.4, 8.9 Hz, OCH$_2$CH), 4.61 (t, 1, J=8.9, one of OCH$_2$CH), 4.55 (d, 1, J=16 Hz, one of ArCH$_2$), 4.54 (d, 1, J=4.7 Hz, C—3 H, overlaps with doublet at 4.55), 4.21 (dd, 1, J=4.7, 9.0 Hz, C—4H), 4.17 (dd, J=7.4, 8.9 Hz, one of OCH$_2$CH), 4.14 (d, 1, J=16 Hz, one of ArCH$_2$).

Anal. Calcd for C$_{27}$H$_{24}$N$_2$O$_3$: C, 76.39; H, 5.70. Found: C, 76.53; H, 5.69.

By using the method described in Example 1, the imine prepared from benzylamine and 3-(2-furyl)-acrolein was condensed with 4(S)-phenyloxazolidin-2-one-3-ylacetyl chloride to provide 1-benzyl-3β-[4(S)-phenyloxazolidine-2-one-3-yl]-4β-[2-(2-furyl)ethenyl]-azetidine-2-one: mp 181°-182° C.; $[\alpha]_D^{20}=+13.6°$ (c=1.6, CHCl$_3$), IR (CHCl$_3$) 3020, 1760, 1660, 1500, 1460, 1410 cm$^{-1}$; $^1$H NMR (CDCl$_3$) δ7.45-7.07 (m, 11, ArH), 6.39 (dd, 1, J=1.8, 3.3 Hz, OCH=CH), 6.27 (d, 1, J=16 Hz, N—CH—CH=CH), 6.25 (d, 1, J=3.3 Hz, O—C=CH), 5.75 (dd, 1, J=16, 8.9 Hz, N—CH—CH=CH), 4.91 (dd, 1, J=8.8, 7.4 Hz, OCH$_2$CH), 4.65 (t, 1, J=8.9 Hz, one of OCH$_2$CH), 4.61 (d, 1, J=15 Hz, one of ArCH$_2$), 4.55 (d, 1, J=4.8 Hz, C—3 H), 4.20 (dd, 1, J=7.4, 8.8 Hz, one of OCH$_2$CH), 4.11 (dd, 1, J=4.8, 8.9 Hz, C—4H), 4.02 (d, 1, J=15 Hz, one of ArCH$_2$).

Anal. Calcd. for C$_{25}$H$_{22}$N$_2$O$_4$: C, 72.44; H, 5.35. Found: C, 72.44; H, 5.41.

1-Benzyl-3β-[(S)-4-phenyloxazolidin-2-one-3-yl]-4β-[2-(3-methoxyphenyl)ethyl]azetidin-2-one The 3-methoxystyryl substituted azetidinone prepared as described in Example 1 (0.552 g, 1.22 mmol) was hydrogenated (balloon pressure) in dichloromethane (20 mL) over 0.052 g of 5% Pd on carbon for 3 hours at room temperature. Filtration through celite and removal of solvent under reduced pressure afforded 0.555 g (100%) of the corresponding 4β-[2-(3-methoxyphenyl)-ethyl]azetidinone (compound 8) as a white solid. Recrystallization from hexane-ethyl acetate gave long needles: mp 134°-135° C.; $[\alpha]_D^{23}+38.6°$ (c=2.2, CHCl$_3$); IR (CHCl$_3$) 3010, 1755, 1605, 1590, 1410 cm$^{-1}$; $^1$H NMR δ7.44-6.42 (m, 14, ArH), 4.97-4.84 (br t, 1, OCH$_2$CH), 4.68 (t, 1, J=9 Hz, one of OCH$_2$), 4.64-4.59 (br d, 1, C$_3$H), 4.32 (s, 2, ArCH$_2$), 4.27 (dd, 1, J=6.4, 9.0 Hz, one of OCH$_2$), 3.77 (s, 3, OCH$_3$), 3.57 (dt, 1, J=6.6, 4.9 Hz, C$_4$H), 2.36 (br t, 1, J=8 Hz, ArCH$_2$CH$_2$), 1.56-1.44 (br q, 1, ArCH$_2$CH$_2$).

Anal. Calcd for C$_{20}$H$_{24}$N$_4$O$_6$: C, 73.66; H, 6.18. Found: C, 73.48; H, 6.11.

Methyl 5-[3β-(t-butyloxycarbonylamino)azetidin-2-one-4β-yl]-3-oxopentanoate

Lithium wire (0.548 g, 79 mmol) was added to 55 ml of ammonia at −78° C. and the mixture was warmed briefly to affect solution of the metal and then recooled to −78° C. under positive argon pressure. The dark blue solution was first treated with tert-butanol (12 mL). A solution of the 1-benzyl-3β-(4-phenyloxazolidin-2-one-3-yl)-4β-[2-(3-methoxyphenyl)ethyl]azetidin-2-one (2.36 g, 5.17 mmol) in THF:tert-butanol (24 mL of a 3:1 mixture) was then added via cannula over a period of 5 minutes. After stirring for exactly 30 additional minutes, dry benzene (2 mL) was added. The blue color discharged after ca. 1 minutes. Ammonium acetate (6.08 g, 79 mmol) was added, the cold bath removed, and the bulk of the ammonia was distilled off through a mercury bubbler. Solvent and any residual ammonia were removed under reduced pressure at 40° C. The remaining white solid was suspended in 50 mL of THF:H$_2$O (1:1), acidified to pH 8 with 3N HCl, and treated with di-tert-butyl dicarbonate (1.8 mL, 7.8 mmol). The two phase mixture was stirred rapidly for 12 hours and then partitioned between dichloromethane (200 mL) and H$_2$O (50 mL). The aqueous phase was reextracted with dichloromethane (50 mL) and the combined organic phases were washed with 50 mL of saturated aqueous NaHCO$_3$, dried (Na$_2$SO$_4$), and concentrated. Chromatography of the residue on 110 g of silica with 40% hexanes in ethyl acetate afforded 1.23 g of the partially purified dihydroaromatic 3β-t-butyloxycarbonylamino-4β-[2-(5-methoxycyclohex-1,4-diene)ethyl]-azetidine-2-one as a waxy solid.

The diene product was dissolved in 25 mL of 50% methanol in dichloromethane, treated with one drop of pyridine and ca. 1 mg of Sudan III dye (Aldrich Chemical Co.), and ozonolyzed at −78° C. until the red color discharged. Dimethyl sulfide (3 mL) was added, the cold bath removed, and the reaction mixture stirred at room temperature for 5 hr. The light orange solution was poured into 100 mL of brine and extracted with dichloromethane (1×200 mL, 1×50 mL). The combined organic layers were dried (Na$_2$SO$_4$) and concentrated. Chromatography of the residue on 65 g of silica with 7% isopropanol in dichloromethane afforded methyl 5-[3β-(t-butyloxycarbonylamino)azetidin-2-one-4β-yl]-3-oxopentanoate (0.97 g, 60% from 8) as an off-white solid. Recrystallization from toluene gave colorless needles: mp 122°-123° C.; $[\alpha]_D^{20}+48.6°$ (c=1.4, CHCl$_3$); IR (CHCl$_3$) 3430, 3420, 3340 (br), 3020, 2990, 1770, 1720, 1510, 1370, 1250, 1160 cm$^{-1}$; $^1$H NMR (CDCl$_3$) δ 6.51 (br s, 1, NH of β-lactam), 5.50 (br d, 1, BocNH), 5.05-4.98 (m, 1, C—3H), 3.83-3.71 (m, 1, C—4H), 3.75 (s, 3, OCH$_3$), 3.48 (s, 2, COCH$_2$CO), 2.74–2.56 (m, 2, CH$_2$CH$_2$CO), 1.93–1.74 (m, 2, CH$_2$CH$_2$CO), 1.45 (s, 9, tert-butyl).

Anal. Calcd. for C$_{14}$H$_{22}$N$_2$O$_6$: C, 53.49; H, 7.06. Found: C, 53.56; H, 7.11.

The 3-t-BOC-aminoazetidinyl β-keto ester prepared as described above was then converted to the 3-hydroxy-1-carba(1-dethia)-3-cephem ester by the procedures of the following Example 1.

EXAMPLE 1

Benzyl 7β-(t-butyloxycarbonylamino)-3-trifluoromethylsulfonyloxy-1-carba(1-dethia)-3-cephem-4-carboxylate

A. Diazo Transfer

To a 0° C. solution of the β-keto ester (1.13 g, 3.6 mmol) in 10 mL of acetonitrile was added p-toluenesulfonyl azide (3.6 mL of a 1.5M solution in dichloromethane) and diisopropylethylamine (0.13 mL, 0.75 mmol). The reaction was covered with foil, stirred at room temperature for 2 hours, and then partitioned between dichloromethane (100 mL) and brine (50 mL) containing 10 mL of 0.5M tartaric acid. The aqueous layer was reextracted with dichloromethane (50 mL) and the combined organic layers dried (Na$_2$SO$_4$) and concentrated. Chromatography of the residue on 100 g of silica with 5% isopropanol in dichloromethane afforded 1.15 g (94%) of the diazo keto ester as a white solid. Recrystallization from ethyl acetate-hexanes gave small needles: mp 136°–137° (dec); [α]$_D^{20}$+65.8° (c=0.6, CHCl$_3$); IR (CHCl$_3$) 3440, 3420, 3360 (br), 3020, 2990, 2150, 1770, 1720, 1650, 1510, 1440, 1370, 1320, 1160 cm$^{-1}$; $^1$H NMR δ 6.49 (br s, 1, NH of β-lactam); 5.46 (d, 1, J=8.6, BocNH); 5.06 (dd, 1, J=4.8 Hz, 8.1 Hz; C$_3$H); 3.85 (s, 3, OCH$_3$); 3.85–3.78 (m, 1, C$_4$H); 3.06–2.82 (m, 2, CH$_2$CH$_2$CO); 2.0–1.75 (m, 2, CH$_2$CH$_2$CO); 1.45 (s, 9, tert-butyl).

Anal. Calcd. for C$_{14}$H$_{20}$N$_4$O$_6$: C, 49.40; H, 5.92. Found: C, 49.47; H, 5.93.

B. Transesterification

A solution of benzyl alcohol (20 mL, 193 mmol) and titanium isopropoxide (0.78 mL, 2.62 mmol) was stirred under vacuum (1 mm Hg) for 45 minutes to remove isopropanol. The flask was covered with foil, vented to argon, and the diazo β-keto methyl ester (0.953 g, 2.80 mmol) was added. the solution was heated at 36° C. for 42 hours, diluted with 60 mL of diethyl ether, and treated with saturated aqueous Na$_2$SO$_4$ (3 mL). The mixture was stirred rapidly overnight, and then filtered through a pad of celite. After removal of ether on a rotary evaporator, the benzyl alcohol was distilled off using a kugelrohr oven (15 millitorr, 50° C.). Chromatography of the residue on 100 g of silica afforded the corresponding diazo β-keto benzyl ester (0.837 g, 72%) as a white solid: mp 152–153 (dec); [α]$_D^{20}$+55.6° (c=0.7, CHCl$_3$); IR (CHCl$_3$) 3450, 3420, 3350 (br), 3020, 2990, 2150, 1770, 1715, 1655, 1510, 1370, 1305, 1165 cm$^{-1}$; $^1$H NMR δ 7.45–7.3 (m, 5, ArH), 6.4 (br s, 1, NH of β-lactam), 5.40 (d, 1, J=8.6, BocNH), 5.26 (s, 2, ArCH$_2$), 5.06 (br dd, 1, J=4.5 Hz, 8.5 Hz; C$_3$H), 3.79 (dt, J=4.5, 8.5 Hz, C$_4$H), 3.05–2.82 (m, 2, CH$_2$CH$_2$CO); 2.0–1.73 (m, 2, CH$_2$CH$_2$CO), 1.45 (s, 9, tert-butyl).

Anal. Calcd. for C$_{20}$H$_{24}$N$_4$O$_6$: C, 57.68; H, 5.81. Found: C, 57.57; H, 5.74.

C. Cyclization Rhodium (II)

A solution of the diazo β-keto benzyl ester (0.12 g, 0.29 mmol) in 6 mL of alumina filtered chloroform was heated to reflux and treated with rhodium (II) acetate dimer (1.5 mg, 0.0034 mol). After heating for 20 minutes, the mixture was placed in an ice bath, and treated sequentially with diisopropylethyl amine (0.10 mL, 0.6 mmol) and trifluoromethanesulfonic anhydride (0.049 mL, 0.29 mmol). The reaction was maintained at 0° C. for 15 minutes and then partitioned between dichloromethane (75 mL) and 0.5M aqueous tartaric acid (25 mL). The organic layer was dried (Na$_2$SO$_4$) and concentrated to a light red oil, which was chromatographed on 20 g of silica with 6% ethyl acetate in dichloromethane to afford benzyl 7β-(t-butoxycarbonylamino)-3-trifluoromethsulfonyloxy-1-carba(1-dethia)-3-cephem-4-carboxylate (0.118 g, 78%) as a hard, colorless foam: [α]$_D^{20}$+31.5° (c=0.5, CHCl$_3$); IR (CHCl$_3$) 3420, 3010, 2990, 1790, 1725, 1505, 1435, 1250, 1160, 1140 cm$^{-1}$; $^1$H NMR (CDCl$_3$) δ 7.46–7.3 (m, 5, ArH), 5.39 and 5.25 (two d (AB), 2, J=12.1 Hz, ArCH$_2$), 5.22–5.10 (m, 2, BocNH and C$_7$H), 3.86 (dt, 1, J ca. 4.2, 11.9 Hz, C$_6$H), 2.63 (dd, 2, J=4.0, 8.8 Hz, C=CCH$_2$), 2.20–2.08 and 1.78–1.60 (m, 2, CH—CH$_2$), 1.44 (s, 9, tert-butyl).

Anal. Calcd. for C$_{21}$H$_{23}$N$_2$F$_3$O$_8$S: C, 48.46; H, 4.45. Found: C, 48.61; H, 4.49.

EXAMPLE 2

Benzyl 7β-phenoxyacetylamino-3-trifluoromethylsulfonyloxy-1-carba(1-dethia)-3-cephem-4-carboxylate To a solution of the 7β-t-butoxyaminocarbacephalosporin (0.12 g, 0.23 mmol) prepared as described in Example 6, in 1 mL of anisole was added 2 mL of trifluoroacetic acid. After 30 minutes the solution was concentrated under reduced pressure (1 mm Hg) to an off-white solid. Phenoxyacetic anhydride (0.094 g, 0.33 mmol) and dichloromethane (2.5 mL) were added to the solid, the mixture cooled to 0° C. and treated with diisopropylethyl amine (0.13 mL, 0.75 mmol). The solution was stirred for 30 minutes and then partitioned between 0.5N aqueous tartaric acid (50 mL) and dichloromethane (75 mL). The organic phase was washed with saturated aqueous NaHCO$_3$, dried (Na$_2$SO$_4$), and concentrated to an oil. Chromatography on 20 g of silica gel with 6% ethyl acetate in dichloromethane afforded 0.115 g (90%) of benzyl 7β-phenoxyacetylamino-3-trifluoromethanesulfonyloxy-1-carba(1-dethia)-3-cephem-4-carboxylate as a hard foam: [α]$_D^{23}$+35.8° (c=0.6, CHCl$_3$); IR 3420, 3040, 1790, 1740, 1695, 1605, 1525, 1500, 1435, 1250 cm$^{-1}$; $^1$H NMR (CDCl$_3$) δ 7.45–6.88 (m, 11, ArH and NH), 5.45–5.23 (m, 3, AB of ArCH$_2$ and C—7H), 4.54 (s, 2, ArOCH$_2$), 3.94 (ddd, J=3.5, 5.1, 11.7 Hz, C—6H), 2.65–2.57 (m, 2, CHCH$_2$CH$_2$), 2.10–1.98 and 1.70–1.54 (m, 2, CHCH$_2$CH$_2$).

EXAMPLE 3

7β-(2-thienylacetylamino)-3-trifluoromethylsulfonyloxy-1-carba-3-cephem-4-carboxylic acid p-Nitrobenzyl 7β-amino-3-trifluoromethylsulfonyloxy-1-carba-3-cephem-4-carboxylate is acylated in methylene chloride with 2-thienylacetyl chloride in the presence of propylene oxide and then is deesterified to provide the title compound.

EXAMPLE 4

7β-(D-Phenylglycylamino)-3-trifluormethylsulfonyloxy-1-carba-3-cephem-4-carboxylic acid 7β-[D-2-(t-Butyloxycarbonylamino-2-phenyl)-acetamido]-3-hydroxy-1-carba-3-cephem-4-carboxylic acid benzyl ester is reacted with triflic acid anhydride in the presence of triethylamine to form the t-BOC protected 3-trifluoromethylsulfonyloxy ester. The t-butyloxycarbonyl protecting group is removed with p-toluenesulfonic acid and the benzyl ester is removed with aluminum chloride and anisole to provide the title compound.

EXAMPLE 5 p-Nitrobenzyl 7β-Phenoxyacetylamino-3-chloro-1-carba(dethia)-3-cephem-4-carboxylate A solution of 240 mg of p-nitrobenzyl 7β-phenoxyacetylamino-3-trifluoromethylsulfonyloxy-1-carba(dethia)-3-cephem-4-carboxylate and 500 mg of lithium chloride in 3 ml of DMF was heated at 80° C. for 5.5 h. The reaction mixture was then cooled, diluted with ethyl acetate, washed with water and with brine, dried over magnesium sulfate, and concentrated by evaporation. The concentrate was chromatographed over silica gel and the product eluted with methylene chloride-ethyl acetate. Evaporation of the eluate gave 112 mg of the title compound as a yellow foam. The product was further purified by rechromatography over silica gel.

EXAMPLE 6

7β-Phenoxyacetylamino-3-chloro-1-carba(dethia)-3-cephem-4-carboxylic acid

Benzyl 7β-phenoxyacetaylamino-3-trifluoromethylsulfonyloxy-1-carba(dethia)-3-cephem-4-carboxylate was heated at 80° C. in DMF with excess lithium chloride to yield the corresponding 3-chloro-3-cephem benzyl ester. The benzyl ester group was removed with aluminum trichloride and anisole to provide the title compound.

EXAMPLE 7

7β-[2-(2-aminothiazol-4-yl)-2-methoxyiminoacetamido]-3-trifluoromethylsulfonyloxy-1-carba-3-cephem-4-carboxylic acid syn-2-(2-Triphenylmethylthiazol-4-yl)-2-methoxyiminoacetyl chloride is reacted in acetonitrile with benzyl 7β-amino-3-trifluoromethylsulfonyloxy-1-carba-3-cephem-4-carboxylate in the presence of triethylamine and the acylation product, benzyl 7β-[2-(2-triphenylmethylaminothiazol-4-yl)-2-methoxyiminoacetylamino]-3-trifluoromethylsulfonyloxy-1-carba-3-cephem-4-carboxylate is treated with formic acid to remove the triphenylmethyl group and with aluminum chloride in anisole to remove the benzyl ester group to provide the title compound.

We claim:

1. A compound of the formula

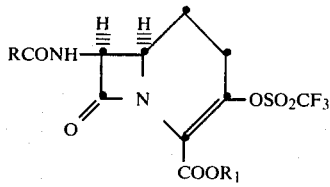

wherein R is hydrogen, $C_1$–$C_6$ alkyl, $C_1$–$C_6$ alkyl substituted by cyano, carboxy, halogen, amino, $C_1$–$C_4$ alkoxy, $C_1$–$C_4$ alkylthio, or trifluoromethylthio; a phenyl or substituted phenyl group represented by the formula

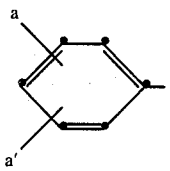

wherein a and a' independently are hydrogen, halogen, hydroxy, $C_1$–$C_4$ alkoxy, $C_1$–$C_4$ alkanoyloxy, $C_1$–$C_4$ alkyl, $C_1$–$C_4$ alkylthio, amino, $C_1$–$C_4$ alkanoylamino, $C_1$–$C_4$ alkylsulfonylamino, carboxy, carbamoyl, hydroxymethyl, aminomethyl, or carboxymethyl; a group of the formula

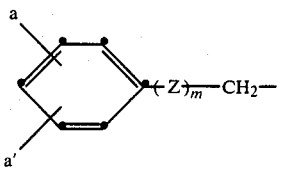

wherein a and a' have the same meanings as defined above, Z is O or S, and m is 0 or 1; a heteroarylmethyl group represented by the formula $R^1$—$CH_2$— wherein $R^1$ is thienyl, furyl, benzothienyl, benzofuryl, indolyl, triazolyl, tetrazolyl, oxazolyl, thiazolyl, oxadiazolyl, thiadiazolyl, and such heteroaryl groups mono-substituted by amino, hydroxy, halogen, $C_1$–$C_4$ alkyl, or $C_1$–$C_4$ alkoxy, or $C_1$–$C_4$ alkylsulfonylamino; a substituted methyl group of the formula

wherein $R^2$ is cyclohex-1,4-dienyl or a phenyl group or substituted phenyl group represented by the formula

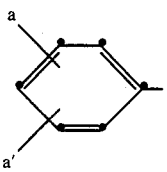

wherein a and a' have the same meanings as defined above, or $R^2$ is $R^1$ as defined above, and Q is hydroxy, $C_1$–$C_4$ alkanoyloxy, carboxy, sulfo, amino, or a substituted amino group of the formula

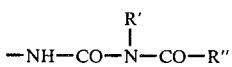

wherein R' is hydrogen or $C_1$–$C_4$ alkyl, and R'' is $C_1$–$C_4$ alkyl, furyl, thienyl, phenyl, halophenyl, nitrophenyl, styryl, halostyryl, nitrostyryl or the group

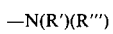

wherein R' has the same meanings as defined above and R''' is hydrogen, $C_1$–$C_3$ alkylsulfonyl, $C_1$–$C_3$ alkyl, or $C_1$–$C_4$ alkanoyl; or Q is a group of the formula

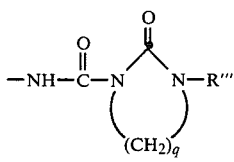

wherein R''' has the same meanings as defined above, and q is 2 or 3; or Q is a group of the formula

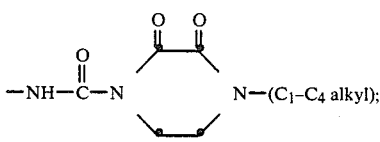

or Q is a benzamido group of the formula

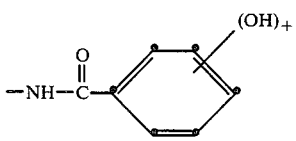

wherein t is 1 to 3; or R is a keto group or an oximino group of the formulae

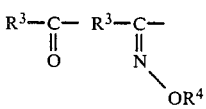

wherein $R^3$ is $R^1$ or $R^2$ as defined above and $R^4$ is hydrogen, $C_1$–$C_4$ alkyl, or a carboxy-substituted alkyl or cycloalkyl group of the formula

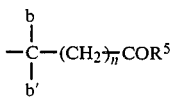

wherein b and b' when taken independently are hydrogen or $C_1$–$C_3$ alkyl, and when taken together with the carbon atom to which they are bonded form a 3- to 6-membered carbocyclic ring, and $R^5$ is hydroxy, $C_1$–$C_4$ alkoxy, amino, $C_1$–$C_4$ alkylamino, or di-($C_1$–$C_4$ alkyl)-amino; $R_1$ is hydrogen or a carboxy-protecting group, and when $R_1$ is hydrogen the pharmaceutically acceptable non-toxic salts thereof.

2. The compound of claim 1 wherein R is a group of the formula

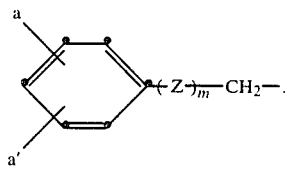

3. The compound of claim 2 wheren Z is 0.

4. The compound of claim 3 which is 7β-phenoxyacetylamino-3-trifluoromethylsulfonyloxy-1-carba-3-cephem-4-carboxylic acid and the pharmaceutically acceptable non-toxic salts thereof.

5. The compound of claim 3 which is 7β-phenylacetylamino-3-trifluoromethylsulfonyloxy-1-carba-3-cephem-4-carboxylic acid and the pharmaceutically acceptable non-toxic salts thereof.

6. The compound of claim 3 wherein $R_1$ is benzyl.

7. The compound of claim 1 wherein R is a group of the formula

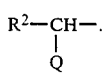

8. The compound of claim 7 wherein $R^2$ is a phenyl or substituted phenyl group.

9. The compound of claim 8 wherein Q is amino, hydroxy or carboxy.

10. The compound of claim 1 wherein R is a keto group or an oximino group of the formulae

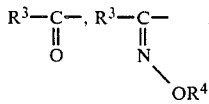

11. The compound of claim 10 wherein R is an oximino group.

12. The compound of claim 10 as the syn isomer.

13. The compound of claim 11 wherein $R^3$ is phenyl, furyl, thiazolyl, or thiadiazolyl.

14. The compound of claim 12 wherein $R^3$ is 2-aminothiazol-4-yl.

15. The compound of claim 13 wherein $R^4$ is $C_1$–$C_4$ alkyl.

16. The compound of claim 1 wherein R is a group of the formula $R^1$—$CH_2$—.

17. The compound of claim 15 wherein $R^1$ is thienyl, furyl, thiazolyl, or thiadiazolyl.

18. The compound of claim 16 wherein $R^1$ is thiazolyl substituted by amino, hydroxy, halogen, or $C_1$–$C_4$ alkyl.

* * * * *

UNITED STATES PATENT AND TRADEMARK OFFICE
CERTIFICATE OF CORRECTION

PATENT NO. : 4,673,737
DATED : June 16, 1987
INVENTOR(S) : David A. Evans and Eric B. Sjogren It is certified that error appears in the above—identified patent and that said Letters Patent is hereby corrected as shown below:

Column 7, second structural formula, "ANH-" should read -- RCONH- --.

Column 9, lines 17-21, the formula appearing as

" 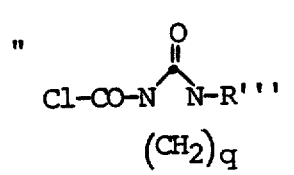 "    should read    -- 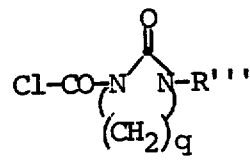 --.

Column 13, line 16, after "trifluoroacetoxy", delete the semicolon and replace with a comma.

Column 15, line 62, "2-furyl)acrolein" should read -- 2-(2-furyl)acrolein --.

UNITED STATES PATENT AND TRADEMARK OFFICE
CERTIFICATE OF CORRECTION

PATENT NO. : 4,673,737
DATED : June 16, 1987
INVENTOR(S) : David A. Evans and Eric B. Sjogren It is certified that error appears in the above—identified patent and that said Letters Patent is hereby corrected as shown below:

Column 20, the structural formula "11a" at line 20 should appear as

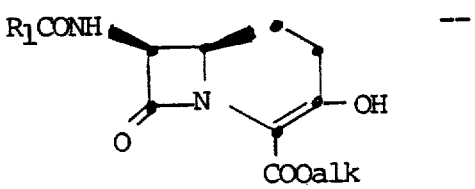

Column 21, line 30, "chloroformat" should read -- chloroform at --.

Column 24, line 17, "(2'200 mL)" should read -- (2 x 200 mL) --.

Column 26, line 29, "minutes" should read -- minute --.

Column 28, line 14, "3-trifluoromethsulfonyloxy-" should read -- 3-trifluoromethylsulfonyloxy- --.

Signed and Sealed this

Twelfth Day of April, 1988

Attest:

DONALD J. QUIGG

Attesting Officer   Commissioner of Patents and Trademarks